US006626830B1

(12) United States Patent
Califiore et al.

(10) Patent No.: US 6,626,830 B1
(45) Date of Patent: Sep. 30, 2003

(54) METHODS AND DEVICES FOR IMPROVED TISSUE STABILIZATION

(75) Inventors: Antonio Califiore, Chieti (IT); David J. Paul, Scotts Valley, CA (US); Eugene Edward Reis, San Jose, CA (US); Harry Leonard Green, II, Santa Cruz, CA (US)

(73) Assignee: Cardiothoracic Systems, Inc., Santa Clara, CA (US)

( * ) Notice: Subject to any disclaimer, the term of this patent is extended or adjusted under 35 U.S.C. 154(b) by 0 days.

(21) Appl. No.: 09/452,760

(22) Filed: Dec. 1, 1999

Related U.S. Application Data

(63) Continuation-in-part of application No. 09/372,661, filed on Aug. 11, 1999, now abandoned, which is a continuation-in-part of application No. 09/305,810, filed on May 4, 1999, now Pat. No. 6,331,158.

(51) Int. Cl.$^7$ .............................................. A61B 17/02
(52) U.S. Cl. ....................................... 600/229; 600/231
(58) Field of Search ................................ 600/206, 210, 600/232, 229, 228, 231, 233

(56) References Cited

U.S. PATENT DOCUMENTS

| | | | |
|---|---|---|---|
| 452,131 A | 5/1891 | Haughawout | 604/289 |
| 810,675 A | 1/1906 | Richter | 600/219 |
| 2,296,793 A | 9/1942 | Kirschbaum | 600/210 |
| 2,590,527 A | 3/1952 | Fluck | 601/7 |
| 2,693,795 A | 11/1954 | Grieshaber | 600/213 |
| 2,863,444 A | 12/1958 | Winsten | 600/214 |
| 3,392,722 A | 7/1968 | Jorgensen | 623/23.68 |
| 3,683,926 A | 8/1972 | Suzuki | 606/154 |
| 3,720,433 A | 3/1973 | Rosfelder | 294/64.1 |
| 3,783,873 A | 1/1974 | Jacobs | 606/151 |
| 3,858,578 A * | 1/1975 | Milo | 600/229 |
| 3,858,926 A | 1/1975 | Ottenhues | 294/64.1 |
| 3,882,855 A | 5/1975 | Schulte et al. | 600/206 |
| 3,983,863 A | 10/1976 | Janke et al. | 600/37 |
| 4,047,532 A | 9/1977 | Phillips et al. | 606/107 |
| 4,048,987 A | 9/1977 | Hurson | 600/206 |
| 4,049,000 A | 9/1977 | Williams | 604/119 |
| 4,049,002 A | 9/1977 | Kletschka et al. | 604/35 |

(List continued on next page.)

FOREIGN PATENT DOCUMENTS

| | | |
|---|---|---|
| DE | 90 04513 | 6/1990 |
| EP | 0 293 760 B1 | 12/1988 |
| EP | 0 293 760 A2 | 12/1988 |

(List continued on next page.)

OTHER PUBLICATIONS

09/345,859 Looney et al. filed on Jul. 1, 1999.
09/438,670 Parsons, et al. filed on Nov. 12, 1999.

(List continued on next page.)

Primary Examiner—Cary E. O'Connor
(74) Attorney, Agent, or Firm—Law Office of Alan W. Cannon

(57) ABSTRACT

Devices and methods are disclosed for accessing and stabilizing an unstable or moving tissue structure within a patient's body, and in particular, for temporarily stabilizing a target site on the beating heart. The devices generally involve tissue stabilizers having at least one multiple link support member operably connecting a stabilizer foot to a retractor. To minimize motion at the stabilizer foot and improve overall stabilization of the target site, the tissue stabilizer may involve the a stabilizer foot having multiple support members connected to the stabilizer foot at discreet locations. To improve the ability of an instrument support member to be easily articulated through an access incision to position the stabilizer foot as desired, the instrument support member may be operable associated with an attachment or mount which provides additional degrees of freedom at the connection to the retractor. A mount construction is disclosed that allows the support member and the articulating mount to be locked using a single knob.

46 Claims, 13 Drawing Sheets

U.S. PATENT DOCUMENTS

| | | | |
|---|---|---|---|
| 4,052,980 A | 10/1977 | Grams et al. | 600/224 |
| 4,226,228 A | 10/1980 | Shin et al. | 600/206 |
| 4,230,119 A | 10/1980 | Blum | 606/194 |
| 4,306,561 A | 12/1981 | de Medinaceli | 606/22 |
| 4,366,819 A | 1/1983 | Kaster | 606/153 |
| 4,368,736 A | 1/1983 | Kaster | 606/153 |
| 4,421,107 A | 12/1983 | Estes et al. | 600/206 |
| 4,428,368 A | 1/1984 | Torii | 601/9 |
| 4,434,791 A | 3/1984 | Darnell | 600/233 |
| 4,461,284 A | 7/1984 | Fackler | 600/228 |
| 4,492,229 A | 1/1985 | Grunwald | 606/148 |
| 4,617,916 A | 10/1986 | LeVahn et al. | 600/228 |
| 4,627,421 A | 12/1986 | Symbas et al. | 600/387 |
| 4,637,377 A | 1/1987 | Loop | 600/37 |
| 4,646,747 A | 3/1987 | Lundback | 600/232 |
| 4,688,570 A | 8/1987 | Kramer et al. | 600/228 |
| 4,702,230 A | 10/1987 | Pelta | 600/234 |
| 4,718,418 A | 1/1988 | L'Esperance, Jr. | 606/5 |
| 4,726,356 A | 2/1988 | Santilli et al. | 600/232 |
| 4,726,358 A | 2/1988 | Brady | 606/243 |
| 4,736,749 A | 4/1988 | Lundback | 600/387 |
| 4,747,395 A | 5/1988 | Brief | 600/210 |
| 4,754,746 A | 7/1988 | Cox | 600/210 |
| 4,803,984 A | 2/1989 | Narayanan et al. | 606/148 |
| 4,808,163 A | 2/1989 | Laub | 604/105 |
| 4,829,985 A | 5/1989 | Couetil | 600/232 |
| 4,852,552 A | 8/1989 | Chaux | |
| 4,854,318 A | 8/1989 | Solem et al. | 606/151 |
| 4,863,133 A | 9/1989 | Bonnell | 248/280.1 |
| 4,865,019 A | 9/1989 | Phillips | 600/232 |
| 4,884,559 A | 12/1989 | Collins | 600/205 |
| 4,925,443 A | 5/1990 | Heilman et al. | 600/61 |
| 4,949,707 A | 8/1990 | LeVahn et al. | 600/234 |
| 4,955,896 A | 9/1990 | Freeman | 606/210 |
| 4,962,758 A | 10/1990 | Lasner et al. | 601/81 |
| 4,971,037 A | 11/1990 | Pelta | 600/234 |
| 4,973,300 A | 11/1990 | Wright | 600/37 |
| 4,989,587 A | 2/1991 | Farley | 600/228 |
| 4,991,578 A | 2/1991 | Cohen | 607/2 |
| 4,993,862 A | 2/1991 | Pelta | 403/59 |
| 5,009,660 A | 4/1991 | Clapham | 606/166 |
| 5,011,469 A | 4/1991 | Buckberg et al. | 604/6.11 |
| 5,025,779 A | 6/1991 | Bugge | 600/217 |
| 5,036,868 A | 8/1991 | Berggren et al. | 128/848 |
| 5,037,428 A | 8/1991 | Picha et al. | 606/155 |
| 5,052,373 A | 10/1991 | Michelson | 600/217 |
| 5,053,041 A | 10/1991 | Ansari et al. | 606/148 |
| 5,080,088 A | 1/1992 | LeVahn | 600/206 |
| 5,098,369 A | 3/1992 | Heilman et al. | 600/16 |
| 5,119,804 A | 6/1992 | Anstadt | 601/153 |
| 5,131,905 A | 7/1992 | Grooters et al. | 600/16 |
| 5,133,724 A | 7/1992 | Wilson, Jr. et al. | 606/151 |
| 5,159,921 A | 11/1992 | Hoover | 600/207 |
| RE34,150 E | 12/1992 | Santilli et al. | 600/232 |
| 5,167,223 A | 12/1992 | Koros et al. | 600/232 |
| 5,171,254 A | 12/1992 | Sher | 606/166 |
| 5,231,974 A | 8/1993 | Giglio et al. | 600/206 |
| 5,287,861 A | 2/1994 | Wilk | 128/898 |
| 5,293,863 A | 3/1994 | Zhu et al. | 600/214 |
| 5,300,087 A | 4/1994 | Knoepfler | 606/207 |
| 5,318,013 A | 6/1994 | Wilk | 600/222 |
| 5,336,252 A | 8/1994 | Cohen | 607/119 |
| 5,382,756 A | 1/1995 | Dagan | 174/92 |
| 5,383,840 A | 1/1995 | Heilman et al. | 600/17 |
| 5,417,709 A | 5/1995 | Slater | 606/205 |
| 5,437,651 A | 8/1995 | Todd et al. | 604/313 |
| 5,452,733 A | 9/1995 | Sterman et al. | 128/898 |
| 5,467,763 A | 11/1995 | McMahon et al. | 600/201 |
| 5,498,256 A | 3/1996 | Furnish | |
| 5,503,617 A | 4/1996 | Jako | |
| 5,509,890 A | 4/1996 | Kazama | |
| 5,512,037 A | 4/1996 | Russell et al. | 600/206 |
| 5,514,075 A | 5/1996 | Moll et al. | 600/202 |
| 5,514,076 A | 5/1996 | Ley | 600/206 |
| 5,520,610 A | 5/1996 | Giglio et al. | 600/233 |
| 5,529,571 A | 6/1996 | Daniel | 600/219 |
| 5,547,458 A | 8/1996 | Ortiz et al. | |
| 5,569,274 A | 10/1996 | Rapacki et al. | 600/158 |
| 5,571,215 A | 11/1996 | Sterman et al. | 623/66 |
| 5,573,496 A | 11/1996 | McPherson et al. | 600/217 |
| 5,607,421 A | 3/1997 | Jeevanandam et al. | |
| 5,607,446 A | 3/1997 | Beehler et al. | 606/198 |
| 5,613,937 A | 3/1997 | Garrison et al. | |
| 5,713,951 A | 2/1998 | Garrison et al. | 623/66 |
| 5,728,151 A | 3/1998 | Garrison et al. | 623/2 |
| 5,730,757 A | 3/1998 | Benetti et al. | |
| 5,735,290 A | 4/1998 | Sterman et al. | 128/898 |
| 5,749,892 A | 5/1998 | Vierra et al. | |
| 5,755,660 A | 5/1998 | Tyagi | 600/205 |
| 5,772,583 A | 6/1998 | Wright et al. | 600/232 |
| 5,782,746 A | 7/1998 | Wright | |
| 5,795,291 A | 8/1998 | Koros et al. | 600/232 |
| 5,799,661 A | 9/1998 | Boyd et al. | |
| 5,807,243 A | 9/1998 | Vierra et al. | |
| 5,813,410 A | 9/1998 | Levin | |
| 5,836,311 A | 11/1998 | Borst et al. | |
| 5,846,187 A | 12/1998 | Wells et al. | 600/201 |
| 5,846,193 A | 12/1998 | Wright | 600/215 |
| 5,846,194 A | 12/1998 | Wasson et al. | 600/228 |
| 5,865,730 A | 2/1999 | Fox et al. | 600/228 |
| 5,868,770 A | 2/1999 | Rygaard | 600/227 |
| 5,875,782 A | 3/1999 | Ferrari et al. | 128/898 |
| 5,876,332 A | 3/1999 | Looney | 606/167 |
| 5,879,291 A | 3/1999 | Kolata et al. | 600/227 |
| 5,882,299 A | 3/1999 | Rastegar et al. | 600/232 |
| 5,885,271 A | 3/1999 | Hamilton et al. | 606/1 |
| 5,888,247 A | 3/1999 | Benetti | 128/898 |
| 5,891,017 A | 4/1999 | Swindle et al. | 600/205 |
| 5,894,843 A | 4/1999 | Benetti et al. | 128/898 |
| 5,899,425 A * | 5/1999 | Corey, Jr. et al. | 248/276.1 |
| 5,906,607 A | 5/1999 | Taylor et al. | 606/1 |
| 5,908,382 A | 6/1999 | Koros et al. | 600/232 |
| 5,927,284 A | 7/1999 | Borst et al. | 128/898 |
| 5,944,658 A | 8/1999 | Koros et al. | 600/232 |
| 5,944,736 A | 8/1999 | Taylor et al. | 606/198 |
| 5,947,125 A | 9/1999 | Benetti | 128/898 |
| 5,947,896 A | 9/1999 | Sherts et al. | 600/229 |
| 5,957,835 A | 9/1999 | Anderson et al. | 600/201 |
| 5,967,972 A | 10/1999 | Santilli et al. | 600/232 |
| 5,967,973 A | 10/1999 | Sherts et al. | 600/233 |
| 5,976,080 A | 11/1999 | Farascioni | 600/213 |
| 5,976,171 A | 11/1999 | Taylor | 606/198 |
| 5,984,865 A | 11/1999 | Farley et al. | 600/213 |
| 5,984,867 A | 11/1999 | Deckman et al. | |
| 6,007,486 A | 12/1999 | Hunt et al. | 600/205 |
| 6,007,523 A | 12/1999 | Mangosong | 604/284 |
| 6,013,027 A | 1/2000 | Khan et al. | 600/201 |
| 6,015,378 A | 1/2000 | Borst et al. | 600/37 |
| 6,017,304 A | 1/2000 | Vierra et al. | 600/204 |
| 6,019,722 A | 2/2000 | Spence et al. | 600/210 |
| 6,027,476 A | 2/2000 | Sterman et al. | 604/96 |
| 6,030,340 A | 2/2000 | Maffei et al. | 600/233 |
| D421,803 S | 3/2000 | Koros et al. | D24/135 |
| 6,032,672 A | 3/2000 | Taylor | 128/898 |
| 6,033,362 A | 3/2000 | Cohn | 600/213 |
| 6,036,641 A | 3/2000 | Taylor et al. | 600/231 |
| 6,050,266 A | 4/2000 | Benetti et al. | 128/898 |
| 6,063,021 A | 5/2000 | Hossain et al. | 600/37 |
| 6,071,295 A | 6/2000 | Takahashi | 606/191 |
| 6,099,468 A | 8/2000 | Santilli et al. | |
| 6,102,853 A | 8/2000 | Scirica et al. | |

| | | |
|---|---|---|
| 6,102,854 A | 8/2000 | Carfier |
| 6,139,492 A | 10/2000 | Vierra et al. ............... 600/204 |
| 6,190,311 B1 | 2/2001 | Glines et al. ............... 600/208 |
| 6,193,652 B1 | 2/2001 | Berky et al. ............... 600/205 |
| 6,200,263 B1 | 3/2001 | Person ....................... 600/227 |
| 6,210,323 B1 | 4/2001 | Gilhuly et al. .............. 600/210 |
| 6,213,940 B1 | 4/2001 | Sherts et al. ............... 600/231 |
| 6,213,941 B1 | 4/2001 | Benetti et al. .............. 600/235 |
| 6,231,506 B1 | 5/2001 | Hu et al. .................... 600/210 |
| 6,283,912 B1 | 9/2001 | Hu et al. .................... 600/232 |
| 6,290,644 B1 | 9/2001 | Green, II et al. ........... 600/235 |
| 6,315,717 B1 | 11/2001 | Benetti et al. .............. 600/210 |
| 6,331,158 B1 | 12/2001 | Hu et al. .................... 600/233 |

FOREIGN PATENT DOCUMENTS

| | | |
|---|---|---|
| EP | 0 293 760 A3 | 12/1988 |
| EP | 0 630 629 | 5/1994 |
| EP | 668 058 A1 | 8/1995 |
| EP | 0 993 806 A2 | 4/2000 |
| FR | 473451 | 1/1915 |
| GB | 168216 | 9/1921 |
| GB | 2 233 561 A | 1/1991 |
| GB | 2 267 827 A | 12/1993 |
| WO | WO 87/04081 | 7/1987 |
| WO | WO 94/14383 | 7/1994 |
| WO | WO 94/18881 | 9/1994 |
| WO | WO 95/01757 | 1/1995 |
| WO | WO 95/15715 | 6/1995 |
| WO | WO 95/17127 | 6/1995 |
| WO | WO 96/00033 | 1/1996 |
| WO | WO 97/10753 | 3/1997 |
| WO | WO 97/26828 | 7/1997 |
| WO | WO 97/32514 A2 | 9/1997 |
| WO | WO 97/32514 A3 | 9/1997 |
| WO | WO 97/40752 | 11/1997 |
| WO | WO 98/27869 | 7/1998 |
| WO | WO 98/48703 | 11/1998 |
| WO | WO 98/49947 | 11/1998 |
| WO | WO 99/08585 | 2/1999 |
| WO | WO 99/09892 | 3/1999 |
| WO | WO 99/16367 | 4/1999 |
| WO | WO 00/06041 | 2/2000 |
| WO | WO 00/10466 | 3/2000 |
| WO | WO 00/16367 | 3/2000 |
| WO | WO 00/42920 | 7/2000 |
| WO | WO 00/42921 | 7/2000 |
| WO | WO 00/42935 | 7/2000 |
| WO | WO 00/42936 | 7/2000 |
| WO | WO 00/42937 | 7/2000 |

OTHER PUBLICATIONS

09/489,274 Brown et al. filed on Jan. 21, 2000.

60/117,333 Looney et al. (provisional) filed on Jan. 24, 1999.

Akins, et al., "Preservation of Interventricular Septal Function in Patients Having Coronary Artery Bypass Graft Without Cardiopulmonary Bypass," American Heart Journal, vol. 107, No. 2, Feb., 1984, pp. 304–309.

Ancalmo, N. and J. L. Ochsner: "A Modified Sternal Retractor," Ann. Thorac, Surg. 21 (1976) 174.

Angelini, G.D., M.D. et al., "Fiber–Optic Retractor for Harvesting the Internal Mammary Artery," Ann. Thorac. Surg. (1990; 50:314–5).

Angelini, G.D., M.D., "Simple, Inexpensive Method of Heart Retraction During Coronary Artery Bypass Surgery," Ann. Thora. Surg 46:46–247, Aug. 1988.

Anstadt, M.D., et al., "Direct Mechanical Ventricular Actuation for Cardiac Arrest in Humans," Chest, vol. 100, No. 1, Jul. 1991.

Antinori, C. et al., "A Method of Retraction During Reoperative Coronary Operations Using the Favaloro Retractor," The Society of Thoracic Surgeons: 1989.

Archer, DO, et al., "Coronary Artery Revascularization Without Cardiopulmonary Bypass," Texas Heart Institute Journal, vol. 11, No. 1, Mar. 1984, pp. 52–57.

Arom, K.V., et al., "Mini–Sternotomy for Coronary Artery Bypass Grafting," The Annals of Thoracic Surgery 1996; 61:1271–2.

Arom, K.V., et al., "Mini–Sternotomy for Coronary Artery Bypass Grafting," The Annals of Thoracic Surgery 1996; 62:1884–85.

Ballantyne, M.D., et al., "Delayed Recovery of Severally 'Stunned 'Myocardium with the Support of a Left Ventricular Assist Device After Coronary Artery Bypass Graft Surgery," Journal of the American College of Cardiology, vol. 10, No. 3, Sep. 1987, pp. 710–712.

Bedellino, M.M., et al., "The Cardiac Rag—Simple Exposure of the Heart," Texas Heart Institute Journal, vol. 15, No. 2, 1988, 134–35.

Beg, R.A., et al., "Internal Mammary Retractor," Ann Thorac, Surg., vol. 39, No. 1, pp. 286–287, Jan. 1985.

Benetti, et al., "Direct Coronary Surgery with Saphenous Vein Bypass Without Either Cardiopulmonary Bypass or Cardiac Arrest," The Journal of Cardiovascular Surgery, vol. 26, No. 3, May–Jun., 1985, pp. 217–222.

Benetti, et al., "Direct Myocardial Revascularization Without Extracorporeal Circulation," Chest, vol. 100, No. 2 Aug., 1991, pp. 312–316.

Bonatti, J., et al., "A Single Coronary Artery Bypass Grafting—A Comparsion Between Minimally Invasive Off Pump Techniques and Conventional Procedures," European Journal of Cardio–Thoracic Surgery, 14 (Supp. I) (1998) S7–S12.

Borst, et al., "Coronary Artery Bypass Grafting Without Cardiopulmonary Bypass and Without Interruption of Native Coronary Flow Using a Novel Anastomosis Site Restraining Device ("Octopus")," J Am Coll Cardiol, May 1996, vol. 27, No. 6, pp. 1356–1364.

Borst, et al., "Regional Cardiac Wall Immunobilization for Open Chest and Closed Coronary Artery Bypass Grafting on the Beating Heart; 'Octopus' Method," Circulation, Oct. 15, 1995, vol. 92, No. 8, supplement 1, 1–177.

British Heart Journal, "Coronary Surgery Without Cardiopulmonary Bypass," pp. 203–205, 1995.

Buffolo, et al., "Direct Myocardial Revascularization Without Cardiopulmonary Bypass," Thoac. Cardiovasc. Surgeon, 33 (1985) pp. 26–29.

Bugge, M., "A New Internal Mammary Artery Retractor," Thorac. Cardiovasc Surgeon 38, pp. 316–317 (1990).

Calafiore, A. M., et al., "Minimally Invasive Coronary Artery Bypass Grafting," The Annals of Thoracic Surgery, 62:1545–8, 1996.

Campalani et al., "A New Self–Retaining Internal mammary Artery Retractor." J. Cardiovas. Surg., vol. 28. (1987).

Cartier, R, MD., "Triple Coronary Artery Revascularization on the Stabilized Beating Heart: Initial Experience," Montreal Heart Institute, CJS, vol. 41, No. 4, pp. 283–288, Aug. 1998.

Chaux, A. and C. Blanche, "*A New Concept in Sternal Retraction: Applications for Internal Mammary Artery Dissection and Valve Replacement Surgery,*" Ann. Thorac. Surg. 42, pp. 473–474, Oct. 1986.

Cooley, D. A., "*Limited Access Myocardial Revascularization,*" Texas Heart Institute Journal, pp. 81–84, vol. 23, No. 2, 1996.

*Correspondence and Brief Communications*, Archives of Surgery—vol. 115, 1136–37, Sep. 1980.

Cremer, J, MD, "*Off–Bypass Coronary Bypass Grafting Via Minithoracotomy Using Mechanical Epicardial Stabilization,*" The Annals of Thoracic Surgery, 63:S79–83, 1997.

Delacroix–Chevalier Surgical Instruments, IMA Saving Packages Brochure.

DelRossi, A J and Lemole, GM, "*A New Retractor to Aid in Coronary Artery Surgery,*" The Annals of Thoracic Surgery, vol. 36, No. 1, 101–102, Jul. 1983.

Fanning, MD., "*Reoperative Coronary Artery Bypass Grafting Without Cardiopulmonary Bypass,*" The Annals of Thoracic Surgery, vol. 55, No. 2, Feb. 1993, pp. 486–489.

Favaloro, M.D., et al, "*Direct Myocardial Revascularization by Saphenous Vein Graft,*" The Annals of Thoracic Surgery, vol. 10, No. 2, Aug. 1970.

Fonger, et al., "*Enhanced Preservation of Acutely Ischemic Myocardium with Transeptal Left Ventricular Assist,*" The Annals of Thoracic Surgery, vol. 57, No. 3, Mar. 1994, pp. 570–575.

Gacioch, et al., "*Cardiogenic Shock Complicating Acute Myocardial Infarction: The Use of Coronary Angioplasty and the Integracion of the New Support Device into Patient Management,*" Journal of the American College of Cardiology, vol. 19, No. 3, Mar. 1, 1992.

Green, GE., "*Technique of Internal Mammary–Coronary Artery Anastomosis,*" The Journal of Cardiovascular Surgery, 78:455–79, 1979.

Groopman, J., "*Heart Surgery, Unplugged; Making the Coronary Bypass Safer, Cheaper, and Easier,*" The New Yorker, Jan. 11, 1999, pp. 43–46, 50–51.

Guzman, F. M.D., "*Transient Radial Nerve Injury Related to the Use of A Self Retraining Retractor for Internal Mammary Artery Dissection,*" J. Cardiovasc. Surg. 30, 1989, pp. 1015–1016.

Hasan, RI, et al., "*Technique of Dissecting the Internal Mammary After Using the Moussalli Bar,*" European Journal of Cardiothoracic Surgery, 4:571–572, 1990.

Itoh, Toshiaki, M.D., et al., "*New Modification of a Mammary Artery Retractor,*" Ann. Thorac. Surg. 9, 1994; 57:1670–1.

Izzat, FRCS, et al., "*Cardiac Stabilizer for Minimally Invasive Direct Coronary Artery Bypass,*" Elsevier Science Inc., 1997 by the Society of Thoracic Surgeons.

Japanese Article "*Heart Retractor*".

Japanese Journal of Thoracic Surgery, vol. 42, No. 2, 1989.

Kazama, S. et al., "*Fabric Heart Retractor for Coronary Artery Bypass Operations,*" The Annals of Thoracic Surgery, 55:1582–3, 1993.

Kolessov, M.D., "*Mammary Artery–Coronary Artery Anastomosis as Method of Treatment for Angina Pectoris,*" Thoracic and Cardiovascular Surgery, vol. 54, No. 4, Oct., 1967, pp. 535–544.

Konishi, T. MD, et al., "*Hybrid–Type Stabilizer for Off- –Pump Direct Coronary Artery Bypass Grafting,*" Annals of Thoracic Surgery 66:961–2, 1998.

Kresh, et al., "*Heart–Mechanical Assist Device Interaction,*" Trans. Am. Soc. Artif. Intern. Organs, vol. XXXII, 1986, pp. 437–443.

Lavergne, et al., "*Transcatheter Radiofrequency Ablation of Atrial Tissue Using a Suction Catheter,*" PACE, vol. 12, Jan. 1989, Part II, pp. 177–186.

Lonn, M.D., et al. "*Coronary Artery Operation Supported by the Hemopump: An Experimental Study on Pigs,*" The Annals of Thoracic Surgery, vol. 58, No. 1, Jul. 1994, pp. 516–523.

Matsuura, A. MD, et al., "*A New Device for Exposing the Circumflex Coronary Artery,*" The Annals of Thoracic Surgery, 59:1249–50, 1995, pp. 1249–1250.

McGee, et al. "*Extended Clinical Support with an Implantable Left Ventricular Assist Device,*" Trans. Am Soc. Artif. Intern. Organs, vol. XXXV, 1989, pp. 614–616.

McKeown, P.P. et al., "*A Modified Sternal Retractor for Exposure of the Internal Mammary Artery,*" Ann. Thorac. Surg. 32 (1981) 619.

Ochsner, JL, et al., "*Surgical Management of Diseased Intracavitary Coronary Arteries,*" The Annals of Thoracic Surgery, vol. 38, No. 4, Jul., pp. 356–362, Oct. 1984.

Parsonnet, V. MD, et al., "*Graduated probes for Coronary Bypass Surgery,* " The Journal of Thoracic and Cardiovascular Surgery, vol. 68, No. 3, 424–26 (Sep. 1974).

Parsonnet, V. MD, et al., "*Self—Retaining Epicardial Retractor for Aortocoronary Bypass Surgery,*" The Journal of Thoracic and Cardiovascular Surgery, 629–30 1979.

Perrault, L. et al., "*Snaring of the Target Vessel in Less Invasive Bypass Operations Does Not Cause Endothelial Dysfunction,*" The Society of Thoracic Surgeons, pp. 751–755, 1997.

Pfister, et al., "*Coronary Artery Bypass Without Cardiopulmonary Bypass,*"The Annals of Thoracic Surgery, vol. 54, No. 6, Dec. 1992, pp. 1085–1092.

Phillips, Steven J., M.D. et al., "*A Versatile Retractor for Use in Harvesting the Internal Mammary Artery and Performing Standard Cardiac Operations,*" J. Thorac. Cardiovasc. Surg. (1989; 97:633–5).

Pilling Surgical Instruments, A Rusch International Company Brochure.

Pittman, John, M.D., et al., "*Improved Visualization of the Internal Mammary Artery with a New Retractor System,*" Ann. Thorac. Surg., 1989; 48:869–70.

Riahi, et al., "*A Simple Technique and Device to Provide a Bloodless Operative Field in Coronary Artery Surgery Without Cross–Clamping the Aorta,*" The Journal of Thoracic and Cardiovascular Surgery, vol. 66, No. 6., Dec. 1973, pp. 974–978.

Richenbacher, M.D., et al., "*Current Status of Cardiac Surgery: A 40–Year Review,*" Journal of American College of Cardiology, vol. 14, No. 3, pp. 535–544.

Robicsek, F., "*Aortic Spoon–Jaw Clamp for Aorta–Saphenous Vein Anastomosis,*" Journal of Cardiac Surgery, 10:583–585, 1995.

Robinson, et al., "*A Minimally Invasive Surgical Method for Coronary Revascularization—Preliminary Experience in Five Patients,*" Circulation, Oct. 15, 1995, vol. 92, No. 8, 1–176.

Rousou, J. et al., "*Cardiac Retractor for Coronary Bypass Operations,*" The Society of Thoracic Surgeons, pp. 52:877–878, 1991.

Roux, D. MD. et al., "*New Helper Instrument in Cardiac Surgery,*" The Annals of Thoracic Surgery, 48: 595–6, 1989.

Roux, D., M.D. et al., "*Internal Mammary Artery Dissection: A Three Dimensional Sternal Retractor*," J. Cardiovasc. Surg., 1989; 30:996–7.

Ruzevich et al. "*Long–Term Follow–up of Survivors of Postcardiotomy Circulatory Support*," Trans. Am. Soc. Artif. Intern. Organs, vol. XXXIV, 1988, pp. 116–124.

Scholz, et al. "*Transfemoral Placement of the Left Ventricular Assist Device 'Hemopump' During Mechanical Resuscitation*," Thoracic and Cardiovascular Surgeon, vol 38 (1990) pp. 69–72.

Stevens, et al., "*Closed Chest Coronary Artery Bypass With Cardioplegic Arrest in the Dog*," $67^{th}$ Scientific Session, 238, I–251.

Trapp and R. Bisarya, "*To Use or Not to Use the Pump Oxygenator in Coronary Bypass Operations*," The Annals of Thoracic Surgery, vol. 19, No. 1, Jan. 1975, pp. 108–109.

Trapp, et al., "*Placement of Coronary Artery Bypass Graft without Pump Oxygenator*," Journal of the Society of Thoracic Surgeons and The Southern Thoracic Surgeons Assn. vol. 19, No. 1, Jan. 1975.

USSC Cardiovascular Thora–Lift J, United States Surgical Corporation, Norwalk, Connecticut, Product Brochure.

Vigano, M., "*Tecnica Operatoria*," Minerva Cardioangiologica, vol. 23–N. 6–7 (1975).

Vincent, J.G., "*A Compact Single Post Internal Mammary Artery Dissection Retractor*," Eur. J. Cardio–Thor. Surg. 3 (1989) 276–277.

Westaby, S. et al., "*Less Invasive Coronary Surgery: Consensus From the Oxford Meeting*," The Annals of Thoracic Surgery, 62:924–31, 1996.

Zumbro, et al., "*A Prospective Evaluation of the Pulsatile Assist Device*," The Annals of Thoracic Surgery, vol. 28, No. 2, Aug., 1979, pp. 269–273.

\* cited by examiner

METHODS AND DEVICES FOR IMPROVED TISSUE STABILIZATION

CROSS-REFERENCE TO RELATED APPLICATIONS

This application is a continuation-in-part of U.S. patent application Ser. No. 09/372,661, filed Aug. 11, 1999, now abandoned, and entitled "Apparatus for Positioning and Securing Surgical Instruments", which is a continuation-in-part of U.S. patent application Ser. No. 09/305,810, filed May 4, 1999 and entitled "Surgical Retractor Apparatus for Operating on the Heart Through an Incision", now U.S. Pat. No. 6,331,158.

FIELD OF THE INVENTION

The present invention relates generally to surgical instruments, and more particularly to methods and devices for improved tissue stabilization using multiple link support members. The tissue stabilizers described herein are particularly useful for stabilizing the beating heart during coronary artery bypass graft surgery.

BACKGROUND OF THE INVENTION

A number surgical procedures require the surgeon to perform delicate operations on tissues within the body that are moving or otherwise unstable. For example, surgeons are routinely performing successful coronary artery bypass graft surgery (CABG) on the beating heart. In a typical coronary artery bypass graft procedure, a blocked or restricted section of coronary artery, which normally supplies blood to a portion of the heart, is bypassed using a source vessel or a graft vessel to re-establish blood flow to the artery downstream of the blockage. This procedure requires the surgeon to create a fluid connection, or anastomosis, between the source or graft vessel and an arteriotomy or incision in the coronary artery. Anastomosing two vessels in this manner is a particularly delicate procedure requiring the precise placement of tiny sutures in the tissue surrounding the arteriotomy in the coronary artery and in the source or graft vessel so that the two may be sutured together.

To ensure that the sutures may be placed with the required accuracy and precision to yield an anastomosis having the desired long term patency, a number of devices have been developed to stabilize a portion of the heart in the vicinity of the target coronary artery. The vast majority of devices suitable for successfully stabilizing the beating heart use either compression or vacuum, or both, to engage and immobilize a portion of cardiac tissue, preferably along opposite sides of the target artery. Devices configured to use a compressive force to stabilize a surgical site on the beating heart can be found, for example, in U.S. Pat. No. 5,894,843 to Benetti et al. Examples of devices configured to use negative pressure or vacuum to stabilize or to assist in stabilizing cardiac tissue are described, for example, in U.S. Pat. No. 5,727,569 to Benetti et al. and U.S. Pat. No. 5,836,311 to Borst et al.

The devices used to stabilize the beating heart must be sufficiently stiff or rigid to resist or placate the movement of the still beating heart muscle as it contracts and relaxes in regular fashion to pump blood throughout the body. Such stabilization devices typically employ a tissue engaging or contacting member and some type of support member to connect the tissue contacting member to a stable support, such as a properly constructed rib or sternal retractor. The support member is most often either a continuous substantially rigid straight or curved shaft or a multiple link member that is sufficiently flexible for positioning and which can be made substantially rigid for stabilization.

Multiple link members typically involve a series of in-line ball and socket links which may be forced together axially by way of a wire or cable extending generally through the center of each link. As the links are forced together, the frictional forces between the successive links increase in proportion to the axial forces supplied by the cable until the frictional forces within the successive ball and socket links along the support member become so great as to resist relative movement therebetween, thus rendering the support member substantially rigid. Examples of articulating members having a plurality of links can be found in European Patent Application EP 0 803 228 A1 published on Oct. 29, 1997 and U.S. Pat. No. 5,899,425.

While the simple operation of multiple link devices have found some acceptance as suitable support members for use in connection with tissue stabilizers, it has proved very difficult to produce the required rigidity and maneuverability required in certain demanding surgical applications, such as stabilizing the beating heart during a CABG procedure. Regarding the rigidity of multiple link devices, for example, a great deal of axial force must be generated to ensure each of the links become sufficiently locked to resist any motion at the surgical site. To support these high loads, the links typically have a much greater diameter than their continuous shaft alternatives thus occupying a greater amount of space in the surgical field.

In addition, the ability to maneuver and position the distal end of a multiple link support member as desired within the surgical field is disadvantaged by the limited range of motion available between successive links along the support member. Attempting to position device through tight turns often proves excessively difficult. For example, a multi-link device may allow each link to rotate only about 15 degrees relative to an adjacent link. With such a configuration, articulating the support member through a 90 degree turn may involve six or more links, thus occupying an excessive amount of space in or near the operative field and resulting in a relatively large radius curve.

Because the rigidity is somewhat inefficient, requiring an increased device size and high forces, and because the maneuverability is limited by the relatively small range of motion between adjacent links, it can be quite difficult to reach and stabilize vessels of the beating heart which are remote from the access opening established by the retractor. Multiple link support members may be unable to develop the rigidity required for optimum stabilization of the peripheral arteries of the beating heart and may be difficult to position at the remote locations which require tight turns or extreme angles of the support member or the contacting member relative to the support member.

Further, when the proximal end of the support member is attached to the retractor in a generally horizontal orientation, it is difficult for a multiple link support member to maneuver the initial roughly 90 degree or less turn required to position the distal end vertically down into the target surgical site. If the multiple link support member is unable to form a sufficiently tight turn or angle relative to its attachment to the retractor, it will tend to occupy an excessive amount of space at the access opening thus blocking visual and instrument access to the target surgical site to be stabilized.

In view of the foregoing, it would be desirable to have a tissue stabilizing device having a tissue contacting member and support member for stabilizing the beating heart which maintains the simplicity of use inherent to multiple links systems but also provides improved maneuverability and rigidity for optimum stabilization. It would also be desirable to have a multiple link support member having a proximal joint or mount which facilitates a sharp turn or angle, such as may be required when the support member is connected proximally to a retractor or other such device.

SUMMARY OF THE INVENTION

The present invention will be described primarily for use during CABG surgery, but the invention is not limited thereto, and is contemplated to be useful for other surgical procedures as well.

The devices and methods of the present invention involve tissue stabilizers which are constructed to provide superior maneuverability and improved tissue stabilization at a target site, for example on the beating heart. The present invention may involve stabilization devices that use at least one multiple link support member to operably connect a stabilizer foot to a stable support, such as a retractor. To minimize motion at the stabilizer foot and improve the overall stabilization of a target site, the present invention may involve a stabilizer foot having two or more multiple link support members. The stabilizer foot is typically positioned as desired at the surgical site with at least one support member connecting the stabilizer foot to a stable support. Subsequently, one or more additional support members may be provided and connected to the stabilizer foot, typically at different locations, to obtain optimum stabilization.

One aspect of the present invention involves an apparatus for stabilizing a coronary artery on a patient's heart comprising a stabilizer foot adapted to engage the surface of the heart, a first support member, and a second support member. The first support member may have a distal end connected to the stabilizer foot at a first distal articulating joint and a proximal end connected to a stable support at a first proximal articulating joint. The second support member preferably has a distal end connected to a second distal articulating joint and a proximal end connected to a stable support at a second proximal articulating joint. The present invention may involve third and, if desired, fourth support members each having separate distal and proximal attachments. Having more than one support member connecting to the stabilizer foot and the stable support at different locations provides greatly improved stabilization.

The stabilizer foot may be configured to have a variety of different distal articulating joints including pinned or rotational joints, ball joints, malleable joints, or the like. In a preferred embodiment, the first or second distal articulating joint is a ball and socket joint, typically formed between a ball or ball-shaped member extending from the stabilizer foot and a mating cavity formed within the most distal link of the first or second support member. The first and second distal articulating joint may also be a rotational joint, typically formed between a generally cylindrical post extending from the stabilizer foot and a mating cylindrical surface provided within the most distal links of the first or second support member. Preferably, the first distal articulating links is a ball and socket joint allowing optimum positioning of the stabilizer foot against the beating heart and the second distal articulating links is a simple rotational joint that facilitates quick attachment of the second support member to the stabilizer foot.

Preferably, the first support member includes a distal link, a proximal link, and a plurality of interconnecting links therebetween. Each of the interconnecting links preferably has a ball or ball-shaped end and a socket or socket-shaped end. The ball shaped ends of the interconnecting links are cooperatively engaged with the socket shaped ends of adjacent interconnecting links thereby forming articulating ball joints between adjacent interconnecting links in a manner that allows the first support member to articulate to varied positions, shapes, or orientations along its length.

Each of the interconnecting links preferably has a central hole through which a flexible wire or cable may be routed. The cable has a distal end connected to the distal link and is routed through the central hole of each of the interconnecting links, preferably exiting through the proximal link. Applying a tensile force to the proximal end of the cable frictionally locks the articulating ball joints between adjacent interconnecting links, thereby causing the support member to become relatively rigid.

The resulting force distribution amongst the multiple support members allows the support members to be configured with relatively small cross-sectional profiles even when the lengths of the support members are quite long. For example, the first support member preferably has a length of greater than about 6.5 inches and an average diameter of less than about 0.5 inches. More preferably, the first support member has a length of about 7.0 inches to about 9.0 inches. The smaller profiles and longer lengths advantageously provide the surgeon with greater visual and instrument access to the surgical site.

The stabilizer foot itself may be adapted to engage the surface of the heart using negative pressure, for example, by way of a vacuum chamber or by way of a plurality of vacuum ports. More preferably, the stabilizer foot has at least one contact surface, preferably textured or otherwise adapted to frictionally engage the surface of the heart. In a preferred embodiment, the stabilizer foot has a first contact surface and a second contact surface, the second contact surface being spaced apart from and oriented substantially parallel to the first contact surface.

Typically, the first and second contact surfaces will be positioned on opposite sides of the target coronary artery. The stabilizer foot may have first and second posts extending about the first and second contact surfaces to which third and fourth support members may be connected. The third and fourth support members have proximal ends connected to the stable support at third and fourth proximal articulating joints, respectively. Preferably, the stable support is a sternal or rib retractor but may be any other stable structure.

Another aspect of the present invention involves an apparatus for stabilizing a coronary artery on a patient's heart which includes a retractor, a mount base operably connected to the retractor, a mount body connected to the mount base at a first articulating joint along a first axis, a multiple link support member, and a stabilizer foot. The proximal end of the support member is preferably operably connected to the mount body along a second axis. The stabilizer foot may be operably connected to the distal end of the support member and adapted to engage the surface of the heart, for example, using friction or negative pressure.

In a preferred embodiment, the first axis is at an angle relative to the second axis, the angle being between about 120 degrees and about 45 degrees, more preferably the angle being about 90 degrees. This dual axis articulation allows optimum access and positioning of the stabilizer foot and support member within the surgical field.

The retractor preferably has opposing retractor blades adapted to engage opposite sides of an access incision. In a preferred embodiment, at least one of the retractor blades further comprises a rail. Preferably, the rail has first and second rail tabs extending therefrom along the length of the rail. Preferably, the mount base is adapted to engage the retractor blade at any desired position along the rail. In a preferred embodiment, the mount base has first and second channels sized to engage the rail tabs. The second channel may be moveable relative to the first channel such that the first and second channels slidably engage the rail tabs when the second channel is in a first position and the channels frictionally grip the rail tabs when the second channel is in a second position.

In a preferred embodiment, the multiple link support member comprises a distal link a proximal link and a plurality of interconnecting links therebetween. Each of the interconnecting links may have a ball or ball-shaped end and a socket-shaped end, the ball-shaped ends being cooperatively engaged with the socket-shaped ends of adjacent interconnecting links thereby forming articulating ball joints between interconnecting links. The distal link preferably has a mating cavity adapted to receive a ball-shaped member extending from the stabilizer foot.

Another aspect of the present invention involves an apparatus for stabilizing the coronary artery which involves a stabilizer foot adapted to engage the surface of the beating heart and a multiple links support member having a proximal end link, a distal end link, and a plurality of center links arranged end-to-end therebetween. The support member preferably has a cable extending through the center links. In a preferred embodiment the distal end link comprises a first member and a second member, the second member having at least first and second portions defining a cavity therebetween for receiving the ball-shaped member. The first member may have a bearing surface adapted to engage at least a portion of the second member to urge the first and second flexible portions together against the ball-shaped member.

The first member preferably has a bore adapted to receive at least a portion of the second member. The distal end of the cable is attached to the second member such that when the second member is pulled in a direction towards the first member by operation of the cable, the first and second flexible portions are engaged by the bearing surface causing them to frictionally engage the ball-shaped member with sufficient force the position of the stabilizer foot relative to the distal end link. In one embodiment, the bearing surface is frustoconical.

The proximal end of the support member is preferably attached to a stable support, which in a preferred embodiment comprises a retractor having opposing retractor blades for engaging opposite sides of an access incision. The stabilizing apparatus may further include a mount base operably connected to the retractor and a mount body connected to the mount base at a first articulating joint along a first axis. The proximal end link is preferably connected to the mount body along a second axis. The first axis may be angled relative to the second axis, the angle being between about 120 degrees and about 45 degrees.

Another aspect of the present invention involves a method for stabilizing a coronary artery on a patient's heart which may comprise the steps of creating an access opening into the patient's thoracic cavity to gain access to the beating heart, providing a stabilizer device having a stabilizer foot operably connected to a support member having a flexible condition and a relatively rigid condition, with the support member in a flexible condition, positioning the stabilizer foot to engage the surface of the heart adjacent the coronary artery, causing the support member to assume the relatively rigid condition to thereby resist movement of the stabilizer foot, providing at least one additional support member, attaching the distal end(s) of the additional support member(s) to the stabilizer foot, and causing the additional support member(s) to assume a relatively rigid condition to thereby provide additional resistance against movement of the stabilizer foot. The access opening is preferably created using a retractor and the method may further include the step of attaching the support member and the additional support member(s) to the retractor.

These and other features of the present invention will become more fully apparent from the following description and appended claims.

DETAILED DESCRIPTION

Figure 1:
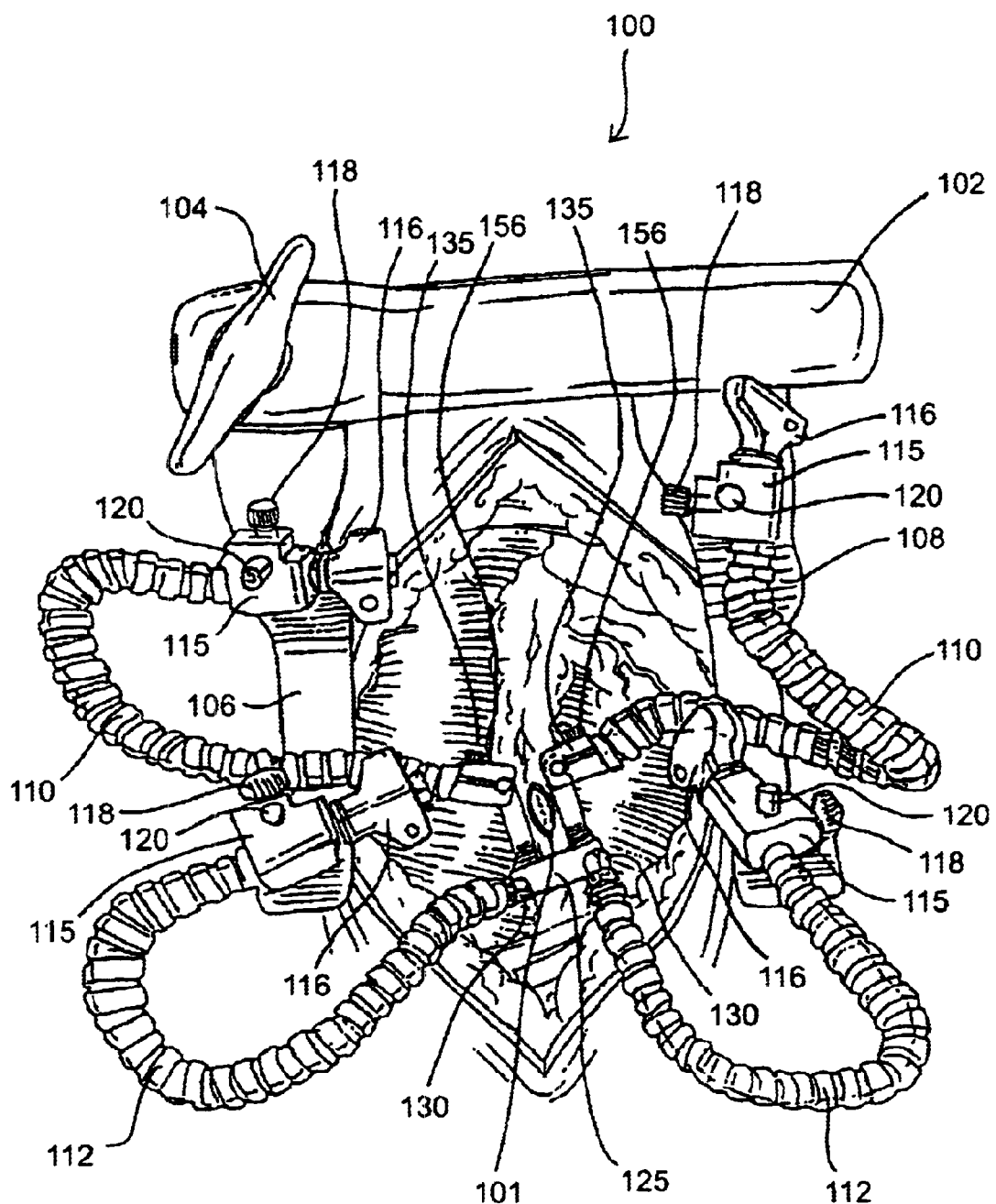
FIG. 1 is a top plan view of a tissue stabilizer system constructed according to the principles of the present invention.

The present invention involves surgical instruments for accessing and stabilizing tissue during a surgical operation and methods for their use. The device described herein may be used in a wide variety of surgical applications that require a tissue structure to be stabilized or immobilized to provide a substantially stable and motionless target surgical field on which a surgical procedure can be performed. By way of example only, the preferred embodiments described in detail below are directed to the stabilization of a portion of the heart to facilitate a surgical procedure on or within the heart, such as a coronary artery bypass graft procedure.

Although the devices and methods of the present invention may have application in both conventional stopped-heart procedures and beating heart procedures, they are preferably used to stabilize the beating heart during a CABG operation which has been specially developed to facilitate completion of an anastomosis, typically between a target coronary artery and a bypass graft or source artery, without requiring cardiac arrest and cardiopulmonary bypass.

A typical beating heart CABG procedure involves accessing the beating heart by way of a sternotomy, mini-sternotomy, thoracotomy, mini-thoracotomy, or other suitable access incision, positioning a tissue stabilizer on, around, or adjacent a coronary artery to stabilize the coronary artery, creating an arteriotomy in the coronary artery, and anastomosing the bypass graft or source artery to the arteriotomy. Typically, the tissue stabilizer has a foot member or heart engaging member at one end for engaging the surface of the beating heart generally using friction, negative pressure, or both. The stabilizer is connected at the other end to a stationary object such as a sternal retractor, rib retractor, or other such stationary structure. Exemplar devices and methods for accessing the beating heart and mounting a stabilizer device are disclosed in co-pending U.S. patent application Ser. No. 09/305,810 "A SURGICAL RETRACTOR APPARATUS FOR OPERATING ON A HEART THROUGH AN INCISION", the entirety of which is herein incorporated by reference.

The devices and methods of the present invention involve tissue stabilizers which are constructed to provide superior maneuverability and improved tissue stabilization at a target site, for example on the beating heart. The present invention may involve stabilization devices that use at least one multiple link support member to operably connect a stabilizer foot to a stable support, such as a retractor. To minimize motion at the stabilizer foot and improve the overall stabilization of a target site, the present invention may involve a stabilizer foot having two or more multiple link support members.

When the stabilizer system is configured to use more than one support member, at least one of the support members may be pre-attached to the stabilizer foot. After the stabilizer foot has been positioned at the target site to be stabilized, the pre-attached support member may be locked in place according to its particular construction to effectuate a significant measure of stabilization or immobilization of the target site. One or more additional support members may then be introduced to the target site, attached to the stabilizer foot, and locked in place to further minimize motion of the tissue at the target site. Although this method of stabilizing a tissue structure will be described in detail below with regard to multiple link support members, it is equally well suited for use with continuous rigid or malleable support members, or a combination of the various types of support members.

To improve the ability of a support member to be easily articulated from its attachment at the stable support to the stabilizer foot positioned at a target site, one or more of the multiple link support members may be operably associated with an attachment or mount which provides additional degrees of freedom at its connection to the stable support. For example, the mount may provide a rotational joint or ball joint at the connection to the stable support so that the proximal link or links of the multiple link support member can be more freely oriented towards the target site, even before any articulation of the links provided by the support member. This tends to result in less visual and instrument obstruction of the surgical site by the support member and allows the stabilizer foot to be positioned at a target site using a support member constructed with fewer links.

A typical construction of the multiple link support members utilizes a series of in-line ball and socket links, each having a significantly limited range of motion. To provide a greater range of motion for adjusting the orientation of the stabilizer foot relative to the support member, the present invention may involve a distal connection to the stabilizer foot which allows a greater range of articulation. The ability to articulate the stabilizer foot through an extended range of motion greatly increases the ability of the device to be satisfactorily positioned at target sites which are remote, angled, or otherwise difficult to reach.

Figure 2:
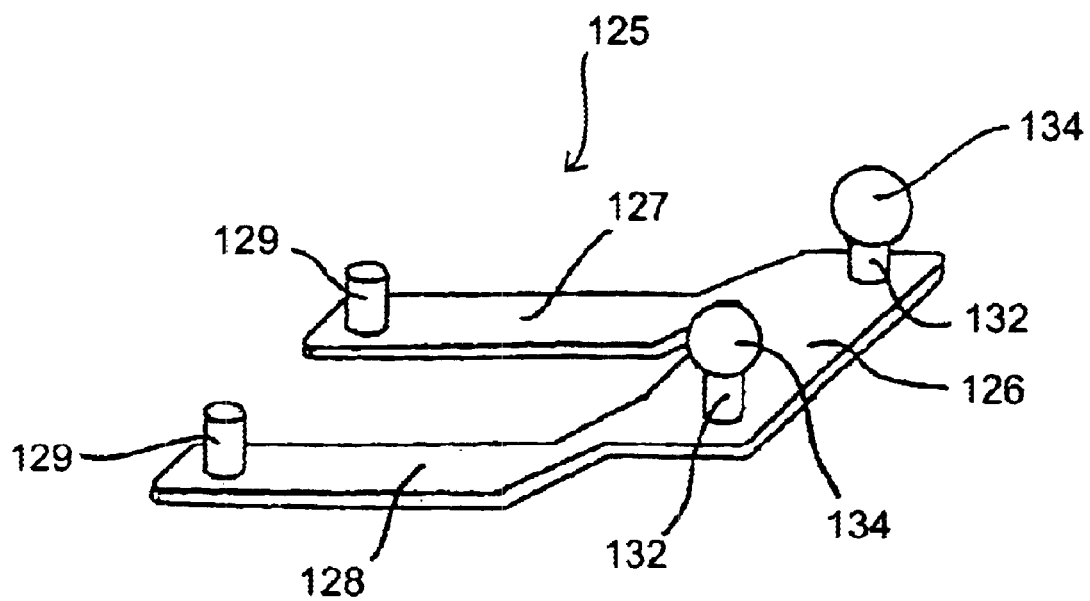
FIG. 2 is a perspective view illustrating the stabilizer foot of the tissue stabilizer system of FIG. 1.
Figure 3:
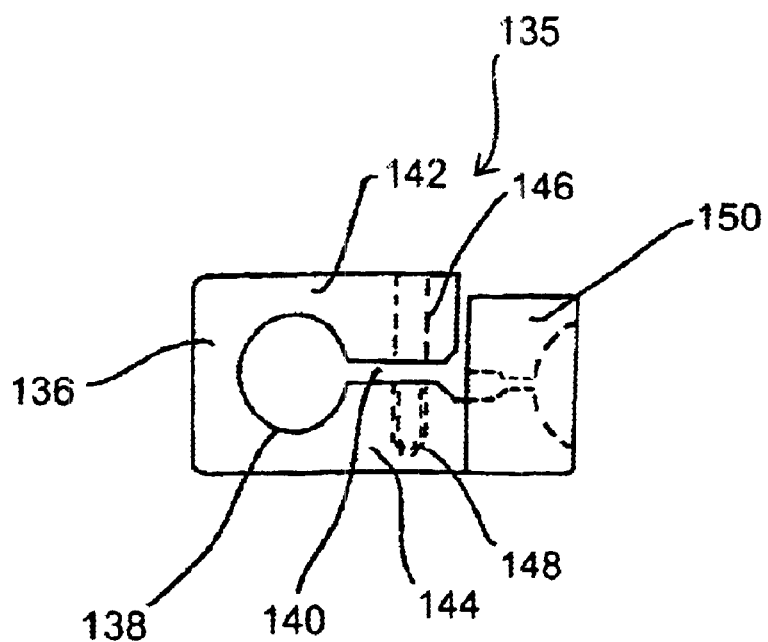
FIG. 3 is top plan view illustrating the distal connector of the tissue stabilizer system of FIG. 1.
Figure 4:
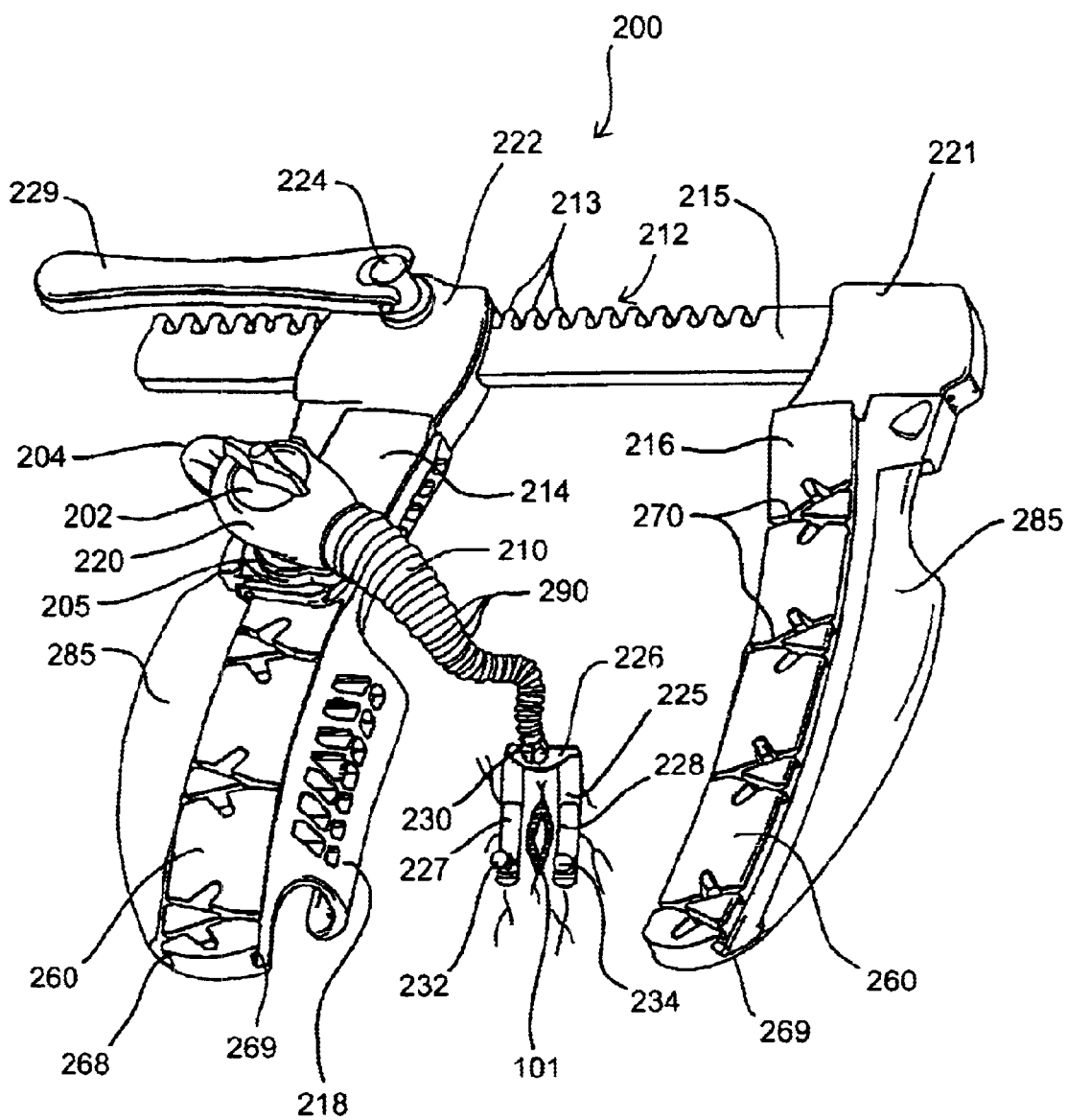
FIG. 4 is a perspective view a tissue stabilizer system constructed according to the principles of the present invention.
Figure 5:
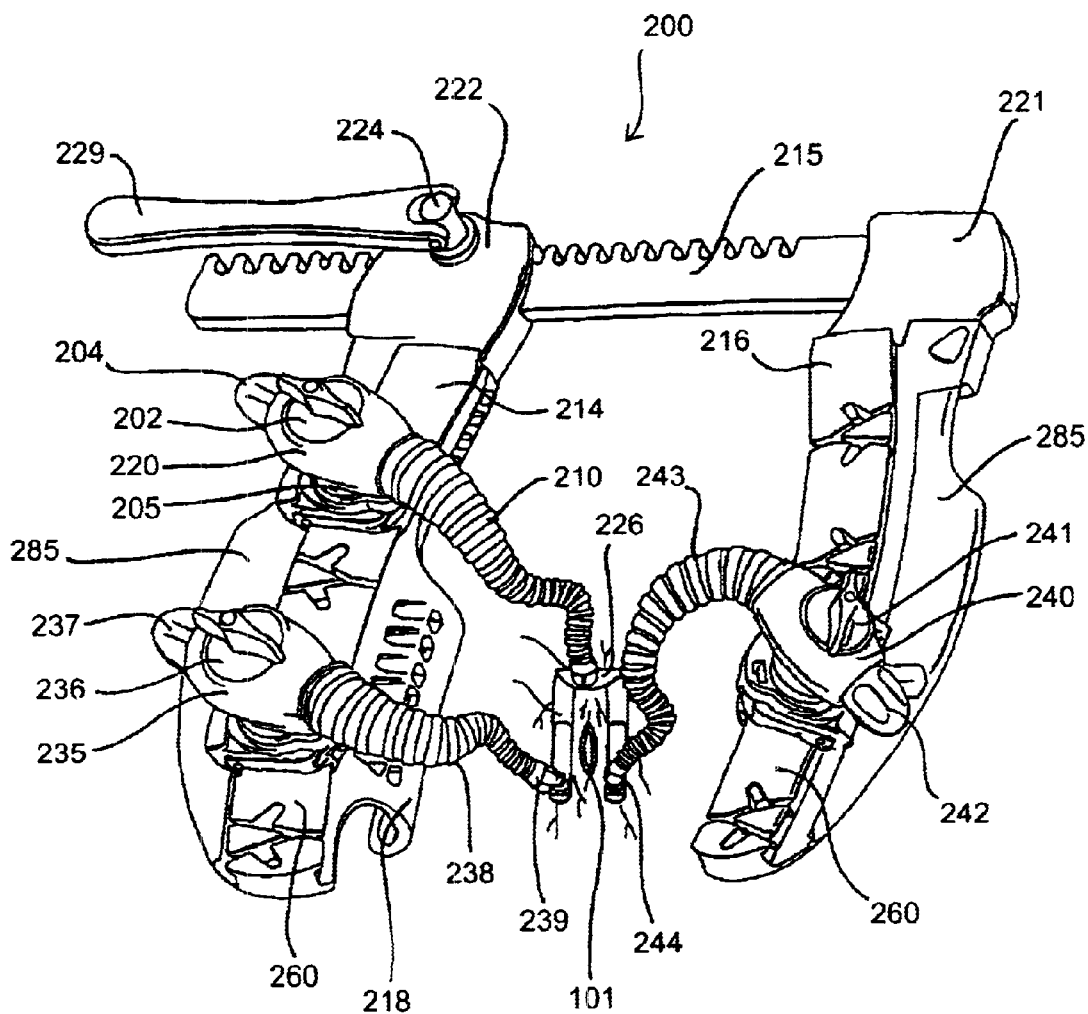
FIG. 5 is a perspective view of a tissue stabilizer system of FIG. 4 illustrating the attachment of additional support members.

Referring to the figures wherein like numerals indicate like elements, an exemplar tissue stabilization system using multiple support members is illustrated with respect to FIGS. 1–3. Tissue stabilization system 100 is shown in place over a coronary artery on the surface of a heart in FIG. 1. Tissue stabilization system 100 generally includes a heart engaging member or stabilizer foot adapted to engage the surface of the heart and one or more support members connecting the foot to a stable support, such as for example retractor 102. Preferably, the stabilizer foot is connected to the stable support using a plurality of multiple link support members. The heart engaging member or stabilizer foot may is preferably configured to a traumatically engage the surface of the heart using mechanical friction, negative pressure, or a combination of the two and may be of any suitable construction.

In a preferred embodiment, stabilizer foot 125 is connected to retractor assembly 102 using multiple link support members 110 and 112. Support members 110 and 112 are preferably a series of interconnecting ball and socket links having a common tension wire or cable (not shown) extending therethrough which may be tensioned to axially compress the ball and sockets together to frictionally lock the individual joints between links. Thus, the position and orientation of support members 110 and 112 may be relatively freely articulated until the cable is tensioned to frictionally engage the individual joints, making the support member relatively stiff or rigid.

In one embodiment, support members 110 and 112 have a proximal housing 115 at which the proximal end of the tension cable may be operably coupled to knob 116. Although not visible in the view shown, knob 116 typically has a threaded portion for engaging a threaded coupling on the proximal end of the tension cable such that rotation of knob 116 relative to housing 115 tensions the cable and compresses the links along support members 110 and 112. Of course, the cable may be tensioned using any other suitable mechanism that can be actuated easily by the user in the context of a surgical setting.

Stabilizer foot 125 preferably has one or more support members which are pre-attached to stabilizer foot 125, and one or more releasable support members which can be connected to stabilizer foot 125 after stabilizer foot 125 has been positioned as desired on the surface of the heart. In a preferred embodiment stabilizer foot 125 has two support members 112 pre-attached at distal ball joint 130, preferably at raised base 126. When stabilizer foot 125 is configured to use two pre-attached support members 112 as shown, the distal ball joints 130 are generally spaced apart a predetermined distance along raised base 126.

If stabilizer foot 125 if configured to use only one pre-attached support member, it may be attached to either one of the two distal ball joints as may be clinically advantageous, or a single center ball joint may be provided. In addition, a single support member may be provided which bifurcates to connect to any two of the provided ball joints as desired. Such a bifurcated support member provides the desirable multiple point mounting at the stabilizer foot with minimal obstruction of the surgical field.

Figure 7:
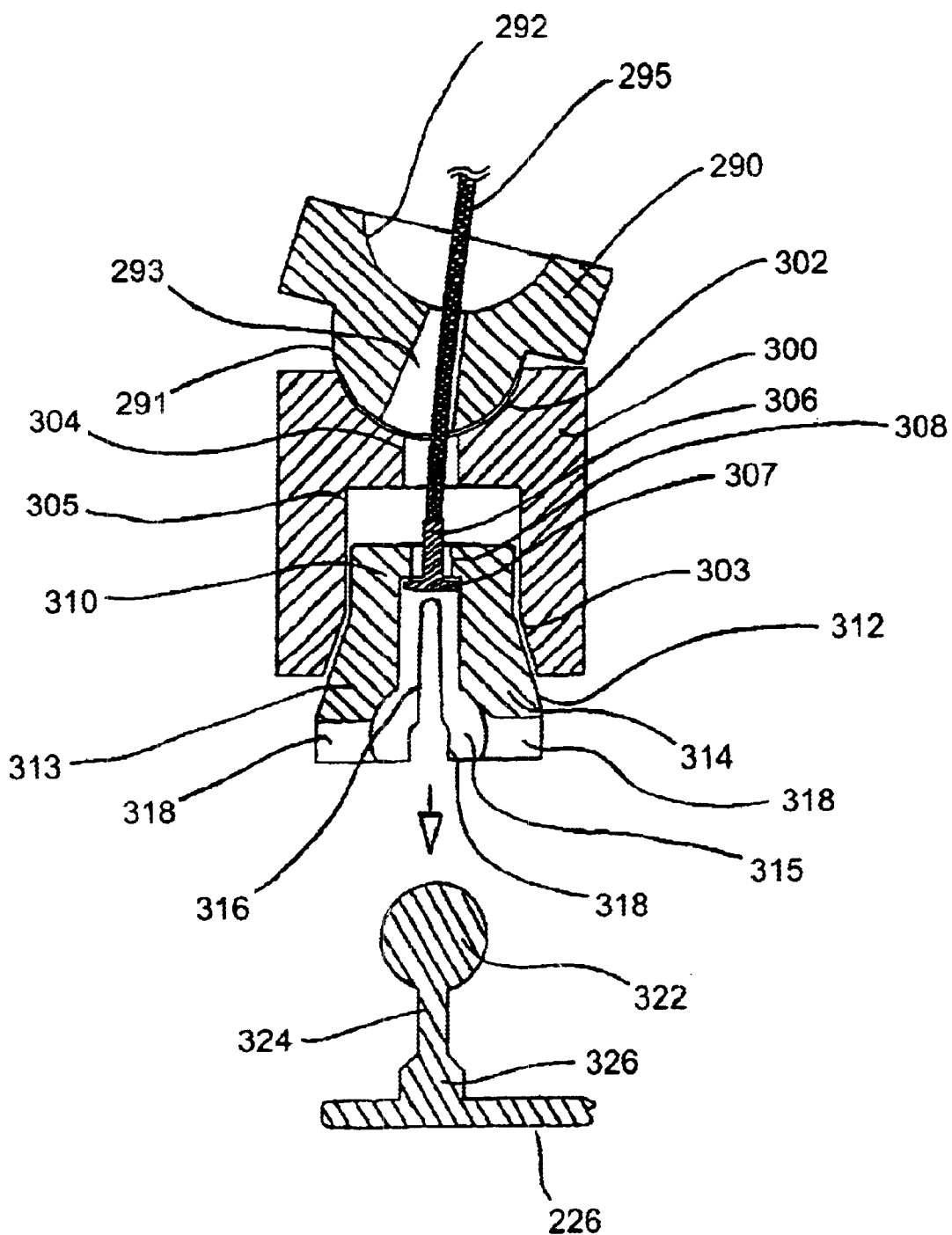
FIG. 7 is a cross-sectional view illustrating a distal ball and socket attachment to a stabilizer foot.

Distal ball joint 130 may be any suitable articulating joint that allows stabilizer foot 125 to be positioned over a target artery as shown and then locked with the support member as tension cable becomes taught. In a preferred embodiment, stabilizer foot 125 may have one or more generally upward extending posts 132 each supporting a ball or ball-shaped member 134 which may be engaged by the distal end of support members 112. In one embodiment, ball shaped member 134 may be conveniently engaged by way of a support member having a distal collet type construction as illustrated in FIG. 7, discussed in detail below.

With support members 112 attached to stabilizer foot 125 in an articulating fashion at distal ball joints 130, stabilizer foot may be placed over the target site as desired. In the case of stabilizing a coronary artery on the beating heart for performing a CABG procedure, stabilizer foot 125 preferably has first and second contact members 127 and 128 which may be placed on opposite sides of a target coronary artery to allow the application of the required stabilization forces to the surrounding or adjacent tissue without significant compression or occlusion of the coronary artery. Once the stabilizer foot has been positioned at the target site, one or both of support members 112 is stiffened or locked using knob 116, thereby providing a significant measure of stabilization to the affected tissue.

In some instances, it may be possible for a single multiple link support member to provide acceptable stabilization. In many cases, however, and especially cases involving the difficult access requirements of multiple vessel bypass procedures on the beating heart, a single multiple link support member cannot achieve sufficient rigidity for optimum stabilization without resorting to excessive forces, disadvantageously short support member lengths, or excessively large support member profiles or diameters. Further, depending on the final articulated position of a particular multiple-link support member, the support member may be better able to resist forces delivered along certain vectors and somewhat less able to resist (i.e., more flexible) forces delivered along other vectors relative to the support member. As a result, having more than one support member attaching at different global relationships to the encountered forces tends to significantly increase the ability of stabilizer foot 125 to resist movement which would otherwise occur as a result of the forces delivered by the contacted tissue.

If the stabilization provided by support members 112 alone is sufficient, the surgical procedure can proceed without further alteration or adjustment of the stabilization system. To further minimize or eliminate motion of stabilizer foot 125 one or more releasable support members 110 may be attached to the front of stabilizer foot 125 using any convenient attachment means. Support members 110 may be attached to a ball and post arrangement similar to that of support member 112. In another embodiment, support members 110 may be have distal connectors 135 which attach to posts 129 preferably extending generally upwardly from contact members 127 and 128.

Preferably, distal connector 135 is constructed to clamp onto post 129 to prevent any relative motion therebetween. Distal connector 135 may have clamp portion 136 connected to link portion 150. Link portion 150 has a socket adapted to receive a ball portion of the distal link of support member 110 and a generally centered counterbore in which the distal end of the tension cable which forces the multiple links into frictional engagement may terminate. Clamp portion 136 has a center bore 138 sized to fit over pin 129 and a slot 140 generally separating clamp portion 136 into first clamp halve 142 and second clamp halve 144. A threaded extension of knob 156 may be assembled through clearance hole 146 and threaded into threaded hole 148. Tightening knob 156 then forces first and second clamp halves 142 and 144 together, thus fixing distal connector 135 relative to post 129. Once connected to support member 125, support members 110 may be locked using knobs 116, preferably acting on a central tension cable (not shown).

The pre-attached support members 112 and the releasable support members 110 are preferably oriented in such a manner as to minimize visual and instrument access to the surgical site. To provide greater flexibility in positioning the support members in a desirable fashion, one or more of the housings 115 may mounted to the stable support using an articulating joint which provides one or more additional degrees of freedom about which housing 115 may be articulated. In one embodiment, housings 115 have a generally cylindrical bore adapted to rotate about mating pins 120 which are fixedly connected to the stable support, in this case retractor assembly 102.

The retractor assembly can be any suitable retractor suitable to create the desired access opening for operating on the heart, or other tissue structure of interest. In a preferred embodiment, retractor assembly 102 has opposing retractor arms 106 and 108 which may be driven apart by a suitable toothed or cable drive actuated by handle 104. Each of retractor arms 106 and 108 have a means for attaching support members 110 and 112, which in the embodiment shown comprise posts 120 which may be rotationally received by cylindrical mating bores in housings 115. In this manner, each of housings 115 and support members 110 and 112 provided may be rotated about posts 120 to obtain nearly any desired orientation. Housings 115 are fixed in place relative to posts 120 by tightening their respective knobs 118 which are threaded into housings 115 to bear against posts 120.

In a preferred method of operating tissue stabilization system 100, opposing retractor arms 106 and 108 are first placed within a suitable incision and actuated to create an access opening through which the beating heart may be directly viewed. Stabilizer foot 125, with support members 112 connected thereto, is positioned over a target site, preferably with contact members 127 and 128 on opposite sides of a coronary artery targeted which is to be anastomosed to a source or graft bypass vessel. With stabilizer foot 125 roughly in position, knobs 118 associated with housings 115 of support members 112 are tightened to prevent further relative motion at post 120. If desired, a suitable compressive force may be manually applied to stabilizer foot 125 using the operator's hand, the support members themselves, or other suitable instrument. Support members 112 may then be locked by actuation of associated knobs 116 to provide a measure of stabilization to the heart tissue and coronary artery.

If further stabilization is desired, one or both of support members 110 may be attached proximally to retractor arms 106 or 108. The distal connectors 135 may then be placed over posts 129 and secured using knobs 156. Respective housings 115 of support members 110 may be locked in place relative to posts 120 using associated knobs 118. Any desired final adjustments may be made to the position or orientation of support members 110, and then support members 110 are locked or made rigid by actuating knob 116. With the site stabilized, an arteriotomy 101 is then created in the target coronary artery and the graft or source vessel is anastomosed to the substantially motionless arteriotomy 101.

Using more than one support member and connecting each to a separate location on the stabilizer foot has a number of advantages. The multiple point mount as just described provides superior stabilization even with support members that are constructed to have a relatively small outer diameter and are constructed to operate using somewhat less force in the central tension cable. In essence, the multiple support member system allows the use of smaller profile or lower force support members than would normally be required to stabilizer a tissue structure such as the beating heart.

The multiple support member system also allows one or more of the support members to be configured to have a longer length than would normally be feasible in single support member systems due to the resulting inability to stabilize attributable to such longer lengths. The long length advantageously allows the body of the support member to be articulated to a position which will not inhibit access to the surgical site, yet still facilitates placement of the stabilizer foot at locations remote from the proximal attachment to the stable support.

The benefits of increased length is even greater when the support member has also been constructed to take advantage a smaller outer diameter. For example, even with support members having a length of 6.5 inches or more the diameters of the individual links may remain quite small, preferably the largest diameter being 0.5 inches or less, more preferably in the range of about 0.250 inches to about 0.50 inches. In a preferred embodiment, the support members are constructed to have a predetermined length in the range of about 7 inches to about 8.5 inches and an average diameter in the range of about 0.375 inches to about 0.5 inches. Again, the capability to adequately stabilize using support members having long lengths and small outer diameters greatly improves the ability of the surgeon to arrange the surgical site for optimum visual and instrument access.

Another tissue stabilization system capable of utilizing more than one support member is illustrated in FIGS. 4–7. Stabilization system 200 generally includes a stable support in the form of a sternal retractor 212 having opposing blades 214 and 216 for creating an access opening, a stabilizer foot for engaging the tissue to be stabilized, and one or more multiple link support members connecting the stabilizer foot to the sternal retractor. Preferably, the support members have proximal mounts that can be moved to any desired position along the length retractor blades. The proximal mounts may also be provided with increased degrees of freedom to allow for optimum adjustment and positioning of the support members and stabilizer foot.

The stabilizer foot can be any type of foot or end member adapted to engage the surface of the heart using, for example, mechanical compression and friction, negative pressure, or any combination of the two. Preferably, the stabilizer foot is adapted to frictionally engage and press against the surface of the heart. In a preferred embodiment, stabilizer foot 225 has first and second contact members 227 and 228 connected by raised base portion 226 which is preferably in the form of a re-curve. An underside region of contact members 227 and 228 preferably has a textured region specifically configured to frictionally engage the surface of the heart.

Stabilizer foot 225 preferably has at least one multiple link support member which preferably has a series of articulating elements or links interconnected together with a tension cable extending through passageways provided in each element or link. In a first state, the multiple links are allowed to freely articulate thus rendering the support member quite flexible, bendable or positionable. In a second state, the support member may be made relatively stiff or rigid by application of an appropriate tension applied to the cable to force the multiple links into frictional engagement with each other. In a preferred embodiment the links are joined together by articulating ball and socket joints.

In a preferred embodiment, stabilizer foot 225 has at least one support member which may be pre-attached to stabilizer foot 225 to facilitate the placement of stabilizer foot 225 within the surgical site and to provide at least initial stabilization of the tissue at the targeted site. Support member 210 preferably has an interconnecting series of ball and socket links 290, each having a generally spherically-shaped socket 292 on one end and a generally ball-shaped member 291 on the other end, the ball-shaped members of one link adapted to engage within the socket of the next link.

Support member 210 connects proximally to a stable support preferably by way of an instrument mount or the like which provides one or more degrees of freedom which are not inline with the proximal links of support member 210. In a preferred embodiment, support member 210 connects proximally to instrument mount assembly 220. Preferably, instrument mount assembly 220 has ball joint 205 about which at least a portion of instrument mount assembly 220 can be articulated to achieve a desirable position and orientation of the proximal end portion of support member 210. Preferably, ball joint 205 has a working axis which is at an angle with respect to the working axis of the ball and socket joints of the proximal links of support member 210. The angle is typically between about 120 degrees and about 45 degrees and is preferably about 90 degrees.

In a preferred embodiment, retractor blades 214 and 216 have top rails 260 upon which instrument mount assembly 220 may be mounted. Top rails 260 preferably have tabs 268 and 269 along the length of rails 260 which may be engaged by hook or channel features or the like provided on instrument mount assembly 220. This allows instrument mount assembly 220 to be positioned at any desirable location along the length of rails 260.

Figure 6:
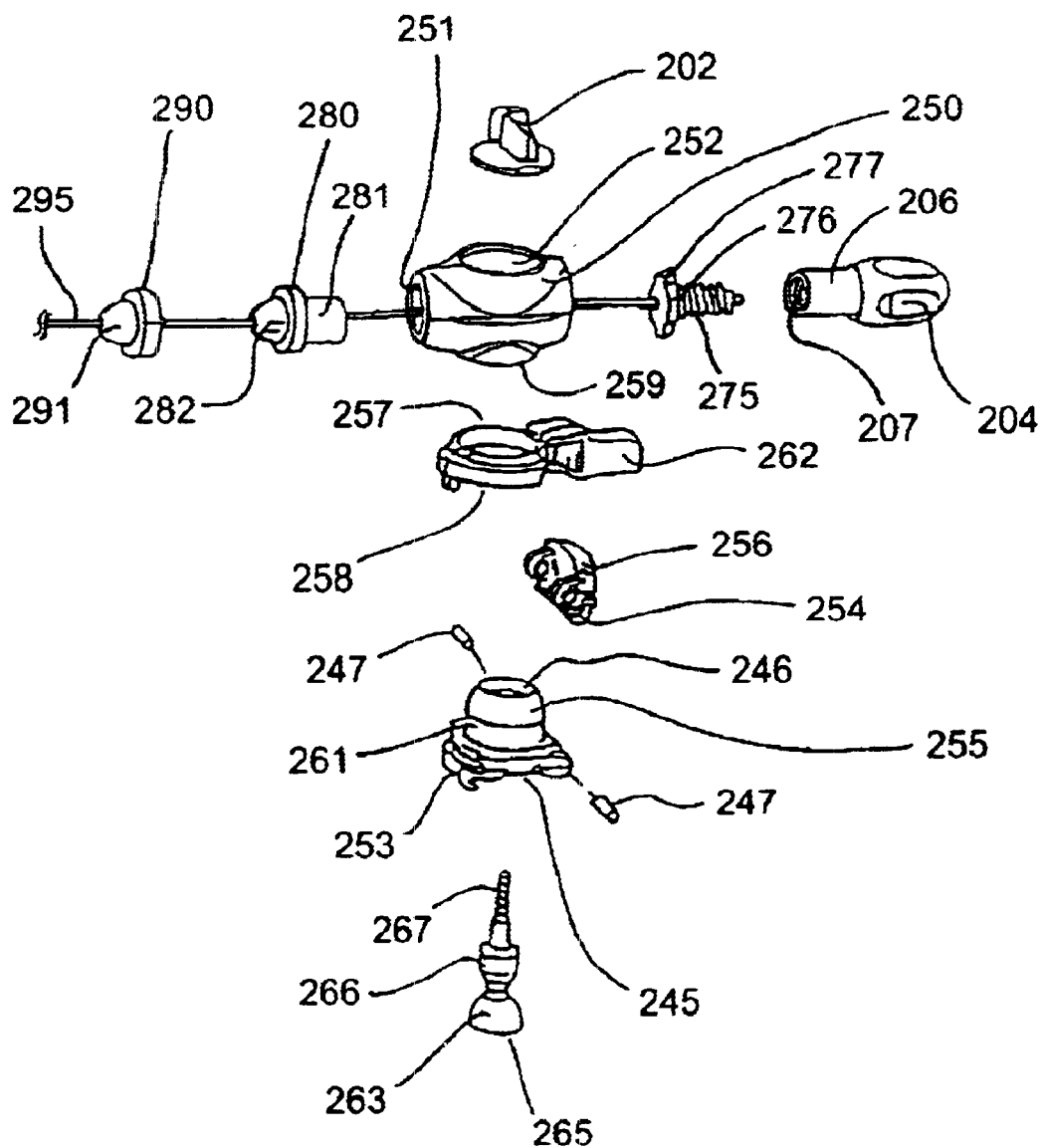
FIG. 6 is an exploded perspective view illustrating the details of the mount assembly of the tissue stabilizer system of FIGS. 4 and 5.

Mount assembly 220 is shown in more detail in FIG. 6. Preferably, instrument mount assembly 220 has a fixed rail grip 253 and a moveable rail grip 254 for engaging tabs 268 and 269. Rail grips 253 is part of mount base 245 and moveable rail grip 254 is part of articulating hinge member 256, which is pivotally attached to mount base 245 by way of hinge pins 247, or other suitable fastener. Mount base 245 is free to controllably slide along rail 260 to any desired position at which point hinge member 256 and rail grip 254 may be articulated in a clamping manner towards rail grip 253 on mount base 245 effectively clamping mount base 245 onto rail 260. Rail grips 253 and 254 are preferably in the form of C-shaped channels sized to receive rail tabs 268 and 269.

Hinge member 256 may be articulated using any suitable mechanism capable of pivoting hinge member 256 to a closed position and holding it there. In a preferred embodiment, hinge member 256 is articulated by action of cam 258. Cam 258 has a bore 257 which cooperatively rotates about cam guide 261 on mount base 245. Base lever 262 may be used to rotate cam 258 about cam guide 261. Additional details and variations of the cam, rail grips and the connection between mount base 245 and rails 260 can be found in U.S. patent application Ser. No. 09/305,810 which has already been incorporated by reference above.

Ball joint 205 is generally created between ball 255 provided at the top of mount base 245 and a socket or mating cavity 259 within mount body 250. Preferably, ball 255 and mating cavity 259 are preferably spherical. Base post 265 extends vertically upward through bore 246 of mount base 245 and vertical bore 252 of mount body 250 until enlarged end portion 263 becomes biased against mount base 245. Top mount knob 202 may then be threaded onto threaded shaft 267 whereby mount base 245 and mount body 250, with ball 255 received within mating cavity 259, becomes captured between top mount knob 202 and enlarged end portion 263. Continued tightening of top mount knob 202 over threaded shaft 267 forces ball 255 harder against mount body 250 until the friction between mating surfaces on ball 255 and mating cavity 259 become so great as to effectively resist any relative movement, thus locking ball joint 205.

As mentioned above a flexible tension wire or cable is preferably routed through the links of support member 210 for the purpose of urging the associated ball and socket joints into frictional engagement rendering support member 210 relatively rigid. In a preferred embodiment, cable 295 passes through each of the links forming support member 210 and then into mount body 250, through transverse bore 266 in base post 265, and terminating at threaded connector 275 which is preferably swaged or otherwise fixedly connected to cable 295. Threaded connector 275 may be engaged by internal threads 207 provided in knob 204. Knob 204 is preferably rotatable relative to mount body 250, and may preferably have a guide housing 206 which is received within a mating bore (not visible in this view) in mount body 250.

With knob 204 engaged against mount body 250, rotation of knob 204 causes internal threads 207 to operate on threaded connector 275 to cause cable 295 to be pulled or released depending on which direction knob 204 was rotated. Threaded connector 275 preferably has an end housing 276 which is keyed against rotation within mount body 250, thus causing the desired linear translation of threaded connector 275 required to tension cable 295. Keying threaded connector 275 against rotation ensures that rotation of knob 204 will result in the desired relative movement between internal threads 207 and threaded connector 275 instead of allowing threaded connector 275 to merely rotate and torsionally wind up cable 295. In a preferred embodiment, end housing 276 is provided with one or more protrusions or keys 277 which mate with keyways (not shown) within mount body 250.

Mount body 250 may engage the proximal most link of support member 210 using any type of convenient fixed, rotational or ball and socket connection. In a preferred embodiment, mount body 250 has a horizontal bore 251 and proximal link 280 of support member 110 has housing 281 which is adapted to rotationally mate with bore 251. Bore 251 and housing 281 may be tapered somewhat so that they more readily frictionally lock as cable 295 is tensioned to compress links 290 as well as proximal link 280 into mount body 250. Proximal link 280 preferably has ball on its distal end which forms a ball and socket joint as it mates with link 290.

Support member 110 is preferably connected distally to stabilizer foot 225 in any convenient manner which allows stabilizer foot 225 to be articulated as required for the surgical procedure contemplated. In one example, stabilizer foot 225 may simply have a socket for receiving ball 291 of the distal most link of support member 110 and cable 295 attaches to and pulls against stabilizer foot 225 to compress the multiple links along support member 110. Articulation of stabilizer foot 225 is then limited to the range of motion provided by that type of ball and socket joint.

Referring to FIG. 7, the distal end of support member 110 is preferably adapted to receive and secure a ball member extending from raised base 226 to stabilizer foot 225 forming a distal ball joint 230. Preferably, raised base 226 has ball 322 extending from post 324. Post 324 may have connecting base 326 to facilitate attachment to raised base 226, for example by welding or by mechanical fasteners or other suitable instrumentality. The distal end of support member 110 preferably has distal member 310 with a socket 315 adapted to mate with ball 322. Because ball 322 and mating socket 315 of distal member 310 are not burdened by having a cable passing through, they may be considerably smaller in size and have an extended range of motion. By also including one or more distal slots 318 leading into the spherical socket sized to accommodate post 324, the range of motion of the stabilizer foot 225 may be further increased. Preferably, distal member 310 has four slots 318 spaced roughly at 90 degree intervals.

In a preferred embodiment, distal member 310 has multiple sections or portions which are constructed to operate in the manner of a collet to lock the position of ball 322 within spherical cavity 315. Preferably, distal member 310 has one or more, preferably two to four, slots 316 extending a distance up the side of distal member 310, forming first and second flexible distal member portions 313 and 314. Slots 316 are preferably configured to provide sufficient flexibility in the structure of distal member 310 to allow distal member portion 313 and distal member portion 314 to flex towards each other, thus causing spherical cavity 315 to collapse around ball 322.

The distal member portions may be urged together in any convenient manner. For example, causing distal member portions 313 and 314 to collapse and lock onto ball 322 may be accomplished by providing collar member 300 just proximal to distal member 310 against which distal member 310 may be urged by operation of cable 295 to force the distal member portions together. In a preferred embodiment, collar member 300 has a proximal spherical socket 302 for receiving ball 291 from link 290 of support member 110 and a central bore 305 for receiving distal member 310. Central bore 305 preferably has an angled or conical bearing surface 303 which mates with a mating angled or conical surface 312 provided on distal member 310. Mating surface 312 extends to a diameter which is greater than the extents of conical surface 303 such that distal member portions 313 and 314 are forced together as mating surface 312 is drawn within conical surface 303.

Distal member 310 is preferably drawn into collar 300 by pulling cable 295 proximally in relation to mount body 250 using knob 204 as described above. Cable 295 is preferably routed through openings 293 provided through each link 290, through opening 304 of collar 300, and attaching distally to distal end member 310. In a preferred embodiment, cable 295 has a cable end member 306 installed through opening 308 in distal end member 310. Cable end member 306 may have flange 307 having a diameter greater than that of opening 308 so that the distal end of cable 295 can pull on distal member 310 with sufficient tension to lock not only distal member 310 onto ball 322 but each of the ball and socket joints along support member 110.

Preferably, distal member portions 313 and 314 spring open far enough in the relaxed state to allow spherical cavity 315 to easily fit over ball 322. This allows the associated support member to be attached to ball 322 and removed from ball 322 as desired. For example, the support member may be detached from ball 322, the stabilizer foot repositioned, and then reattached to ball 322. Also, when a CABG procedure is being performed endoscopically, for example, through small access openings or ports, the stabilizer foot can be positioned onto the heart through a first port or access incision, and one or more additional support members can be inserted through one or more additional access incisions and connected to the stabilizer foot to provide improved stabilization.

In a preferred embodiment of the present invention, support member 210 operates to connect stabilizer foot 225 to instrument mount assembly 220 which may be positioned and fixedly attached to a stable support, such as sternal retractor 212. Sternal retractor 212 may be of any suitable retractor construction as is known in the art, but preferably is of the construction described in U.S. patent application Ser. No. 09/305,810 which has already been incorporated by reference above. Preferably, sternal retractor 212 comprises first and second retractor blades 214 and 216 which are connected to a suitable drive for controllably spreading 214 and 216 apart in a general parallel fashion.

First and second retractor blades 214 and 216 preferably each have at least one channel or sternal engaging member 218 adapted to engage opposite sides of an access incision. Sternal engaging member is preferably U-shaped, curved, or otherwise shaped for securely engaging the incised sternum in a manner that allows very little movement of retractor blades 214 and 216 relative to the incised sternum. As first and second retractor blades 214 and 216 are forced apart, engaging members 218 are correspondingly force the incision open to provide direct access to the desired surgical site. In the example of a sternal approach to the heart, engaging members 218 are adapted to engage each side of the incised sternum to reliably hold and engage the sternum as it is forced open to expose the thoracic cavity and ultimately the heart.

A preferred drive for spreading apart first and second retractor blades 214 and 216 generally includes bar 215 having housing 221 fixed thereto, moveable housing 222 and handle assembly 224 which facilitates movement of moveable housing 222 relative to bar 215. First blade 214 and second blade 216 are preferably operable attached to moveable housing 222 and fixed housing 221, respectively. First and second retractor blades 214 and 216 may be permanently attached or may be removable attached. Retractor blades 214 and 216 may be attached in any suitable fashion including, for example, threaded connections or other mating features on the retractor blades or housing themselves, ordinary or specialized mechanical fasteners, and cam or latching mechanisms adapted to secure the platform blades to the housings. In a preferred embodiment, both moveable housing 222 and fixed housing 221 are constructed with features which engage, secure, and support firs and second retractor blades 214 and 216 in an operable position, this providing assembly 212 which is ready for surgical use.

Bar 215 preferably includes a number of teeth 213 evenly spaced along at least a portion of its length. Handle assembly 224 preferably includes a means for engaging teeth 213 so as to drive moveable housing 222 relative to bar 215 to any desired position under load where it remains so positioned against the load without need for any applied input or holding force. The means for engaging teeth 213 may be any suitable gear, ratchet, cog or like mechanism. Preferably, handle assembly 224 drives moveable housing 222 using one or more drive pins which may successively engage teeth 213 in a cogging manner has handle 229 is rotated by the user.

Platform blades preferably incorporate a number of additional features which enhance the performance of the retractor system such as recessed, locking suture channels 270, flexible tissue retainers 285 and rails 260 to which instrument mount assembly 220 or the like can be mounted. These features are described in further detail in U.S. patent application Ser. No. 09/305,810 which has already been incorporated by reference above.

Tissue stabilization system 200 provides a convenient system with which to position and secure stabilizer foot 225 in desire position and orientation for stabilizing a tissue structure such as a target coronary artery on the surface of the heart. Rails 260 provided on first and second retractor blades 214 and 216 allow as many instrument mounts, each having multiple link support members for attachment to stabilizer foot 225, as may be necessary to be added and positioned along rail 260.

In use, support member 2 is pre-attached to stabilizer foot 225 at distal ball joint 230. Referring again to FIGS. 4 and 5, instrument mount assembly 220 is preferably assembled over rail 260 and positioned to a desired location along rail 260 and locked into place. Stabilizer foot 225 is brought to or near the surgical site and the coronary that is to be stabilized. Ball joint 205 may then be locked in place using top mount knob 202. Stabilizer foot 225 may be further adjusted or oriented relative to the surface of the heart as desired. Support member 210 and distal ball joint 230 are then preferably locked in place using know 204, thus providing a measure of stabilization to the surgical site.

If the stabilization provided by support member 210 alone is sufficient, arteriotomy 101 may be created to begin the standard anastomosis procedure. However, in a preferred embodiment, stabilizer foot 225 is provided with one or more additional post supported ball members to which additional support members, either of the continuous or multiple link type, may be added to provide additional stabilization. In a preferred embodiment, balls 232 and 234 are provided on stabilizer foot 225 near the unsupported end of each of contact members 227 and 228. If additional stabilization is desired, instrument mount assembly 235 having multiple link support member 238 can be brought attached to stabilizer foot 225 at ball 232 to form distal ball joint 239 and secured in place using top mount knob 236 and knob 237.

Even further stabilization can be provided, if desired, by attaching instrument mount assembly 240 having multiple link support member 243 to rail 60 as shown and attaching the distal end of support member 243 to ball 234 to form distal ball joint 244. Support member 243 may be secured in place using top mount knob 240 and knob 242. In one embodiment, stabilization system 200 will have at least one support member attached to rails 60 of both retractor blades 214 and 216. Alternatively, all the support members may be mounted only a single rail or either of retractor blades 214 and 216.

Instrument mount assemblies 235 and 240 are preferably constructed in the same manner as instrument mount assembly 220 described above. Each of the instrument mount assemblies have a ball joint which is not in-line with the cable 295 and the proximal links of the respective support members. This allows the proximal end of each support member to be articulated, oriented, or otherwise directed about the working axis of the ball joint. The ability of the instrument mount to articulate in this fashion allows the stabilizer foot to be more easily placed at a wider range of target surgical sites and greatly alleviates problems associated with the limited range of motion associated with the links from which typical multiple link support members are constructed.

In addition, the additional degrees of freedom provided by the instrument mount assemblies may allow the support members to have constructions which allow improved rigidity or smaller overall size. The ball and socket joints formed by the links of multiple link support members must have sufficient contact area to support the loads required to generate the locking frictional forces. In general, to obtain a greater range of motion in support members having ball and socket joints of a particular diameter, the contact area must typically be decreased due to larger holes through the ball and socket links to accommodate the increased cable travel and due to the smaller degree of engagement between the mating ball and sockets required to gain the increase motion. The articulation provided by the instrument mount assembly may allow at least a portion of the support members to satisfactorily operate with a reduced range of motion, thus allowing a construction having greater contact area or smaller overall size.

The articulation of instrument mount assemblies 220, 235, and 240 may be locked independently by operation of top mount knobs 202, 236, and 241 respectively. In many instances, it may be preferred by the surgeon to have the capability to lock ball joint 205 at a desired position leaving support member 210 free to articulate for positioning stabilizer foot 225 relative to the tissue structure to be stabilized. Further, fine adjustment to the position of stabilizer foot 210 during a surgical procedure may preferably be accomplished by loosening any of knobs 204, 237, or 242 to allow articulation of the respective support member without disturbing the position of the instrument mount.

Figure 8:
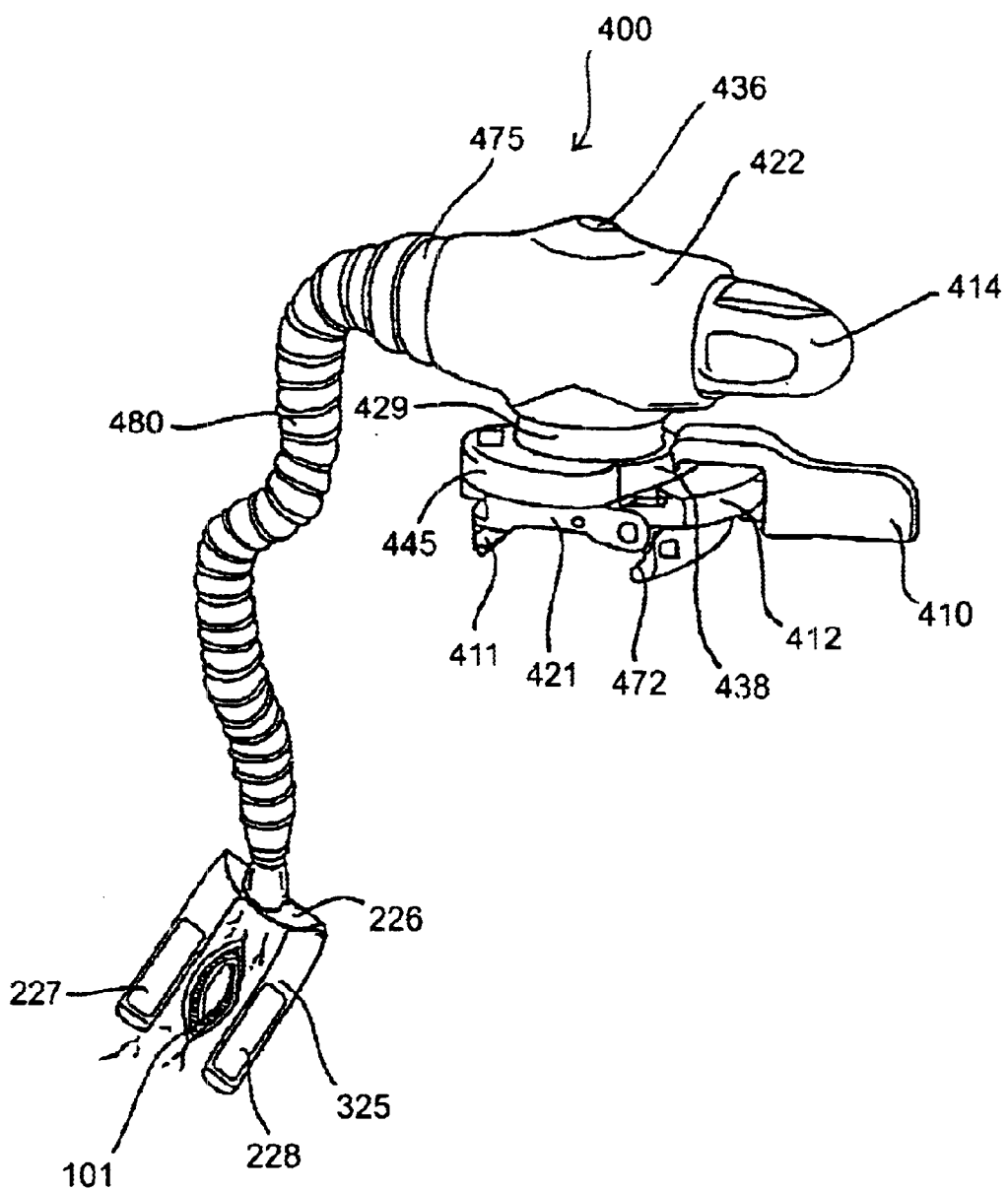
FIG. 8 is a perspective view illustrating a tissue stabilizer system constructed according to the principles of the present invention.
Figure 9:
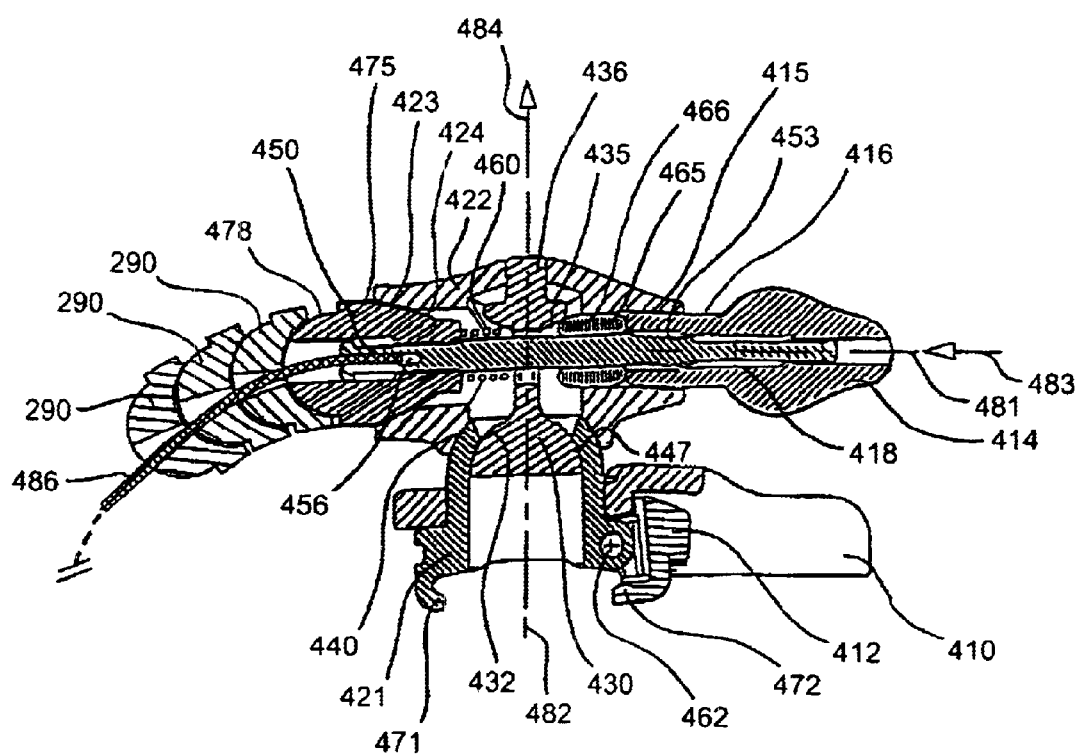
FIG. 9 is a cross-sectional view of a portion of the tissue stabilizer system of FIG. 8.

In other instances, primarily determined by surgeon preference, it may be desirable to tighten all the degrees of freedom using only a single knob, lever, etc. Referring to FIGS. 8 and 9, tissue stabilizer assembly 400 illustrates an instrument mount assembly which allows the various articulating joints provided at stabilizer foot 325, along support member 480, and within instrument mount assembly itself to be locked using a single user interface, such as knob 414. Preferably, the instrument mount assembly allows support member 480 to be operably connected to a stable support, such as a retractor or the like, through an articulating joint that is not in line with the links of support member 480.

The instrument mount assembly preferably has a ball joint between mount base 421 and mount body 422 along a first axis 482 and provides for the connection of the proximal end of support member 480 generally along axis 481. Axis 481 and 482 may be at any convenient angle to each other, typically less than about 120 degrees, more preferably between about 100 degrees and about 45 degrees, and are most preferably generally perpendicular to each other. The ability to lock the articulating joints along the different axis using a single knob tends to reduce the operational complexity of the instrument while maintaining the ability to easily maneuver and secure the stabilizer foot through an access incision and into contact with a tissue structure to be stabilized.

In a preferred embodiment, the articulating joint between mount base 421 and mount body 422 is preferably a ball and socket configuration which may be created between generally spherical ball 429 provided at the top of mount base 421 and a mating cavity or socket 440 within mount body 422 adapted to receive at least a portion of ball 429. Preferably, the ball and socket configuration may also include a generally spherical end 432 on base post 430 which couples with mating surface 447 in the interior of mount base 421.

Base post 430 is generally positioned through mount base 421 such that spherical end 432 abuts mating surface 447 within mount base 421. In this configuration, mount base 421 is controlled between spherical end 432 and socket 440 and becomes locked in place as the distance between spherical end 432 and socket 440 is reduced to a dimension which clamps that portion of mount base 421 residing therebetween. Preferably, base post 430 has an extension or support post 436 which is engaged within a receiving hole in the top of mount body 422 to facilitate the desired controlled motion relative to mount body 422.

Support member 480 preferably has a number of ball and socket elements or links 290 and tension cable 486 extending through passages provided in each link. In a preferred embodiment, the proximal most of links 290 is connected to mount body 422 by way of proximal connecting link 475 which, on a distal end has ball 478 which is engaged within a socket on mating link 290.

Connecting link 475 preferably engages mount body 422 in a manner which allows connecting link 475 to be frictionally locked against mount body 422 as cable 486 is tensioned. The interface between mount body 422 and connecting link 475 may be any suitable connection including a rotational joint or a ball and socket joint. In a preferred embodiment, mount body 422 has a frustoconical surface 423 which mates with frustoconical surface 424 on connecting link 475 to form a rotational joint between mount body 422 and connecting link 475.

The tension in cable 486 may be manually increased of decreased by rotating knob 414 in the appropriate direction. In a preferred embodiment, the proximal end of cable 486 is connected to a pull pin 450. Preferably, the proximal end of cable 486 is positioned within hollow region 456 and secured using a suitable squeezing, crimping, swaging or like process. Pull pin 450 has a threaded section 453 which is engaged by internal threads 418 of knob 414. When the internal threads 418 of knob 414 are advanced along threaded section 453 of pull pin 450 by rotation of knob 414 in the appropriate direction, pull pin 450 and thus cable 486 is pulled in a direction generally opposite to the direction indicated by arrow 483. Urging pull pin in this direction relative to mount body 422 causes the articulating joints along cable 486, including those associated with connecting link 475, to compress and become relatively rigid as the frictional forces reach sufficient magnitude. To prevent pull pin 450 from excessively rotating as knob 414 is rotated, pull pin 450 may be keyed against rotation relative to mount body 422.

At the same time knob 414 is operating to lock support member 480, knob 414 may also be used to drive base post 430 upwards in the direction indicated by arrow 484 to lock the position of mount body 422 relative to mount base 421 as described above. In a preferred embodiment, base post 430 has a lifting or cam surface 435 which may be used to close the position of base post 430 relative to mount body 422 so as to lock the position of mount body 422 relative to mount base 421. Cam surface 435 may be urged upwards along axis 482 by urging a suitable thrust surface in the direction indicated by arrow 483 to engage and lift cam surface 435. The thrust surface is generally associated with knob 414 such that advancement or translation of knob 414 along threaded section 453 of pull pin 450 causes cam surface 435 to move up or down in relation to the position of the mating surface.

The thrust surface may be integral with guide housing 416 of knob 414 or on a separate element which is engaged by knob 414. In a preferred embodiment, cam surface 435 is urged upwards by operation of lifter 465 which slides over pull pin 450, preferably over a non-threaded or smooth section of pull pin 450. Lifter 465 may have a contoured, shaped, radiused, or chamfered thrust surface 466 configured to mate with cam surface 435.

Guide housing 416 of knob 414 is preferably sized to fit within mating guide bore 415 of mount body 422. As knob 414 is tightened, and internal threaded portion 418 is urged along threaded section 453 of pull pin 450, guide housing 416 pushes lifter 465 in the direction indicated by arrow 483, thus engaging cam surface 435 with mating surface 466 causing base post 430 to move upwardly towards mount body 422 and socket 440 in the direction indicated by arrow 484. As with the other articulating joints, tightening knob 414 proportionally increases the frictional forces at the socket 440 ball 429 and spherical end 432/mating surface 447 interfaces until they become functionally locked against relative motion. Compression spring 460 may be provided to pre-load the mechanism so that a minimum amount of frictional forces can be more easily maintained.

The instrument mount assembly of tissue stabilizer assembly 400 may be secured to any suitable stable support and is preferably constructed to cooperatively attach to a sternal or rib retractor having a rail structure as described above with reference to FIGS. 4 and 5. In a preferred embodiment, hinge member 412 having rail grip 472 is pivotally mounted to base 421 by way of pins or the like at hinge mount 462. Cam member 445 may be rotated about cam guide 438 using base lever 410 causing hinge member 412 to urge rail grip 472 towards rail grip 471 on mount base 421, thus facilitating instrument mount 400 to be secured to a rail or other suitable structural component.

A stabilizer foot adapted to engage the surface of the beating heart, preferably using negative pressure, friction, or both, may be connected to the distal end of support member 480 in any manner which provides the necessary degrees of freedom and range of motion to allow the stabilizer foot to be positioned as required by the contemplated procedure. In one embodiment, a stabilizer foot having a ball member associated therewith may be releasably attached to support member 480 in the manner described above with reference to FIG. 7.

Figure 10:
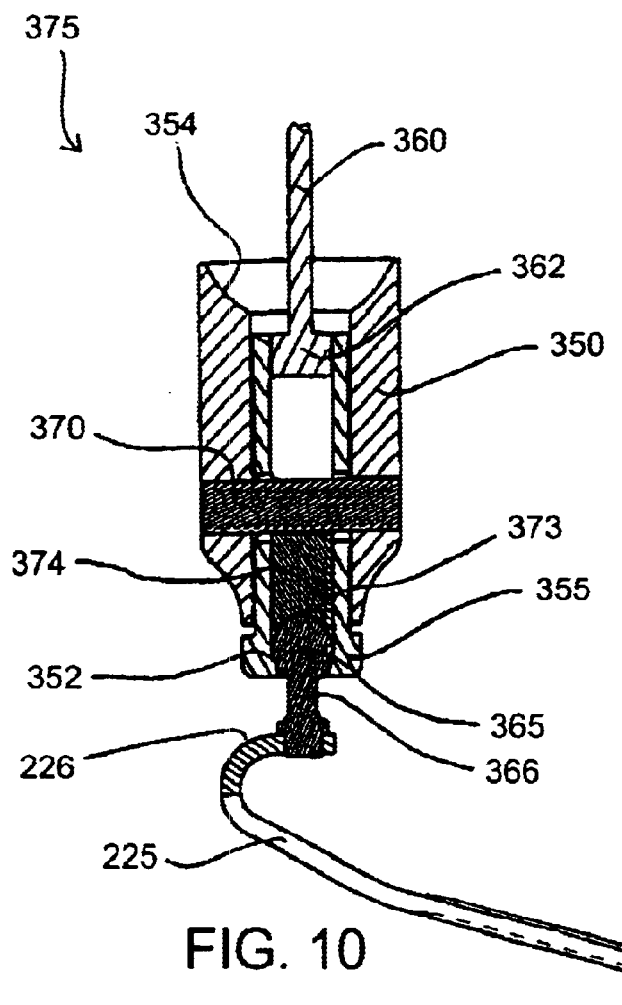
FIG. 10 is a cross-sectional view illustrating one embodiment of a distal connection of a support member to a stabilizer foot.
Figure 11:
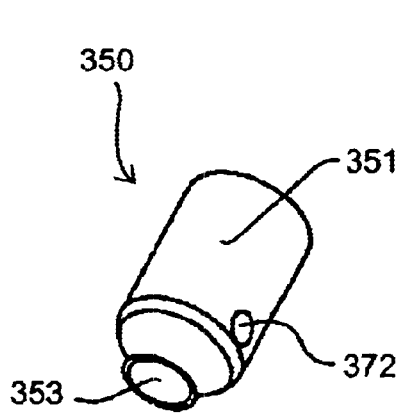
FIGS. 11 and 12 are perspective views illustrating preferred embodiments of the housing and clamp members, respectively, of the distal connection of FIG. 10.
Figure 12:
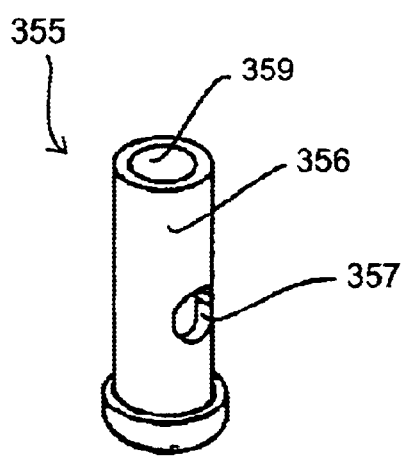

Another distal connection for operably connecting a stabilizer foot having a ball member to a support member is illustrated in FIGS. 10–12. Stabilizer foot 225 preferably has ball 365 extending from post 366 which is in turn securely attached to raised base portion 226. Distal connection 375 preferably allows free rotation of stabilizer foot 225 when in an unlocked state and effectively inhibits or prevents motion between ball 365 and distal connection 375 when in a locked state.

In a preferred embodiment, distal connection 375 includes housing 350, which has a spherical shaped cavity or socket 354 for receiving a mating ball shaped portion of the last ball and socket link of support member 480, and a clamp member 355 moveably disposed relative to housing 350.

Ball 365 is disposed within a cavity or bore 359 within the distal end of clamp member 355 and is engaged by a narrowed portion 352 which may be one or more protrusions or surfaces that are angled, frustoconical, spherical, or like shaped to securely engage a portion of the bottom half of ball 365. The upper portion of ball 365 abuts a portion of housing 350, or a component fixed relative to housing 350, such that relative movement of clamp member 355 in a first direction tends to urge ball 365 against the abutting portion or component of housing 350 to frictionally lock ball 365 between narrowed portion 352 of clamp member 355 and housing 350.

In a preferred embodiment, housing 350 has a main body 351 having main bore 353 extending therethrough. Main bore 353 is sized and configured to slidingly receive body 356 of clamp member 355. Main bore 353 and body 356 are preferably generally cylindrical, although other shapes and configurations which allow clamp member 355 to controllably slide relative to housing 350 are suitable.

The abutting portion or fixed component of housing 350 into which ball 365 is urged by operation of clamp member 355 may be of any suitable extension of housing 350 or other configuration that provides the necessary support to allow the ball to become frictionally locked in place. In a preferred embodiment, clamp member 355 has a central passage or bore 359 into which compression column 374 may be disposed. The distal end 373 of compression column 374 is adapted to frictionally engage a portion of the top half of ball 365 and preferably has a concave shape that is generally conical or spherical. The distal end 373 may optionally include a textured, rubberized, or like portion to enhance friction and thus improve locking.

Movement of compression column 374 relative to housing 350 may be limited or eliminated by way of locking pin 370 which is preferably secured within transverse mating holes 372 of housing 350 by any suitable technique including mechanical threads, adhesives, welding, heat staking, or interference fit. Locking pin 370 passes through passageways or holes 357 which are sufficiently oversized relative to the pin to allow clamp member 355 to translate relative to housing 350 without interference from locking pin 370.

Ball 365 may be positionally locked between clamp member 355 and compression column 374 by urging clamp member 355 towards compression column 374 in any convenient manner. Preferably, a distal end of cable or wire 360 is attached to clamp member 355 which may be tensioned to lock ball 365. Cable 360 is preferably routed through a plurality of ball and socket links which make up all or a portion of a support member as described above. When cable 360 is tensioned, both ball 365 and the links of the support member become frictionally locked against further relative movement. Cable or wire 360 may is preferably attached to clamp member 355 using a crimping process or other suitable technique or fastener. Cable 360 may include a enlarged or collar portion 362 which may crimped into place within central bore 359 of clamp member 355.

Figure 13:
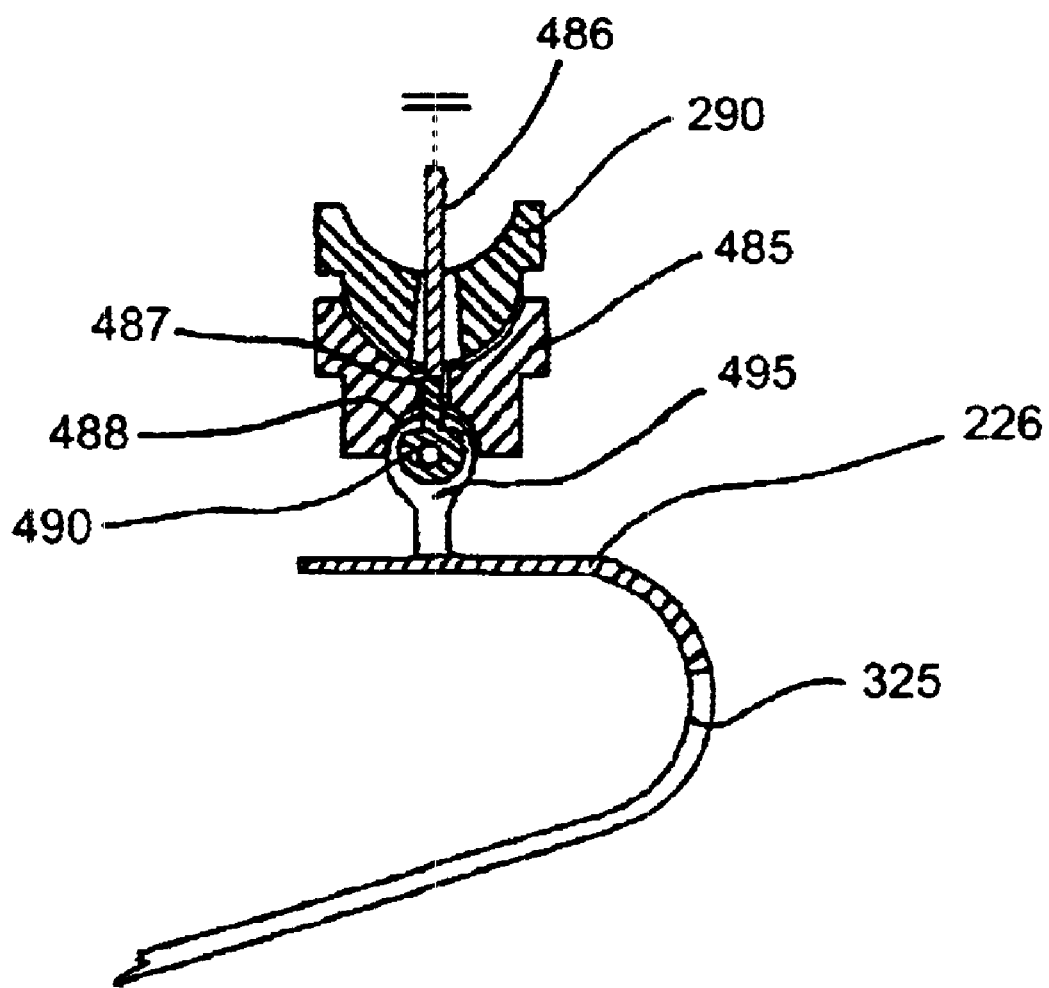
FIG. 13 is a cross-sectional view illustrating a preferred distal connection to a stabilizer foot.
Figure 14:
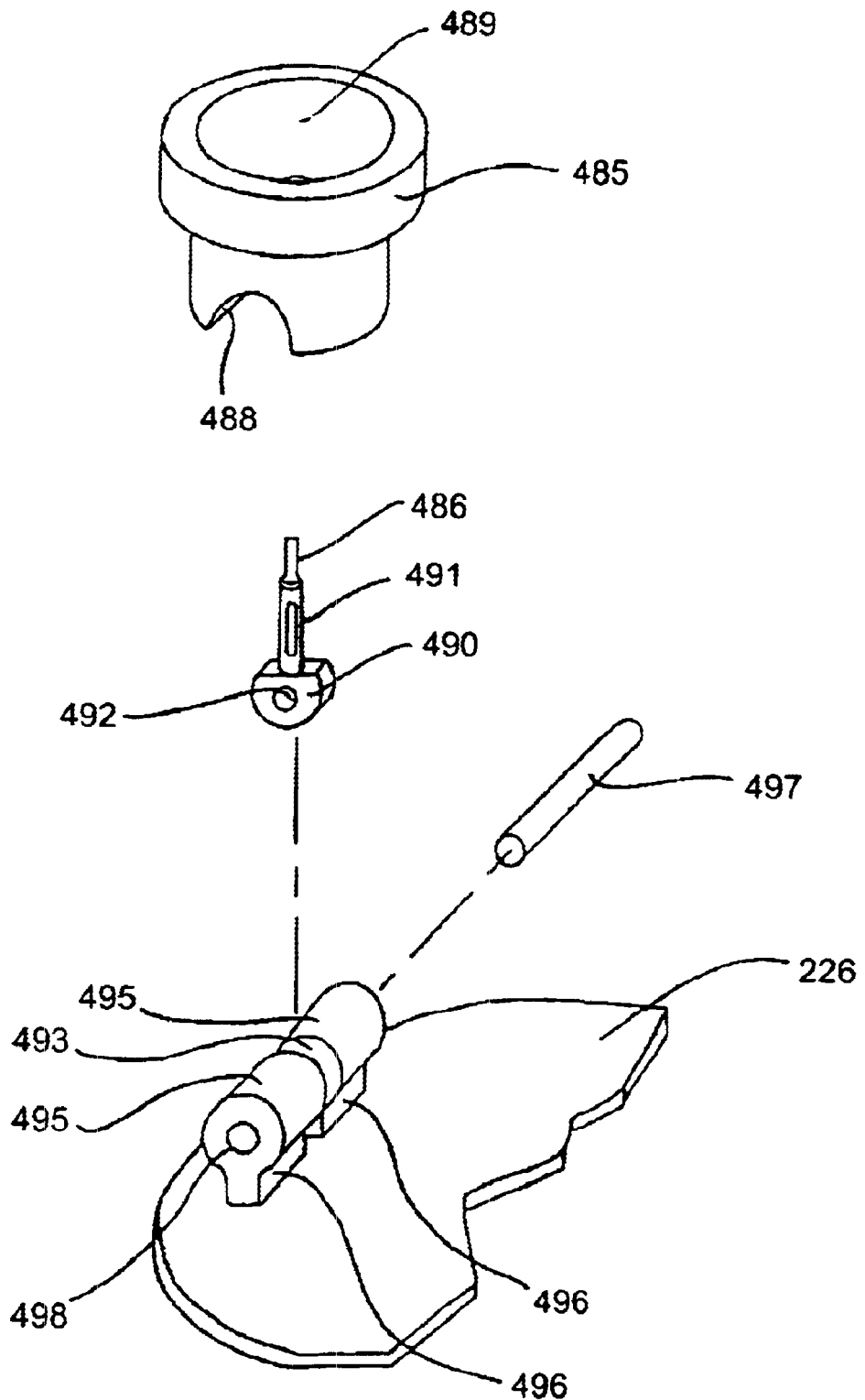
FIG. 14 is an exploded perspective view illustrating the distal connection of FIG. 13.

In some instances, acceptable maneuverability may be achieved with a distal connection having only a rotational degree of freedom at the connection to the stabilizer foot and relying on the degrees of freedom provided by links 290 of support member 480. In a preferred embodiment illustrated in FIGS. 13 and 14, stabilizer foot 325 is provided with pivot boss 495. Pivot boss 495 preferably has a generally cylindrical outer surface about which stabilizer foot 325 may pivot when mated with cooperating cylindrical pivot surface 488 on distal link 485. Distal link 485 has spherical socket 489 adapted to mate with the ball end of link 290 of support member 480. Pivot boss 495 may be connected to base portion 226 of stabilizer foot 325 by way or a post member, rib, or web 496 connected to and extending from base portion 226.

The distal end of cable 486 is preferably connected to stabilizer foot 325 in a manner which will not cause the cable to bend or bind excessively as pivot boss 495 of stabilizer foot 325 rotates within mating surface 488 of link 485. In a preferred embodiment, the distal end of cable 486 is routed through central passage or hole 487 and connected to stabilizer foot 325 using end connector 490 having a cable connecting portion 491 which facilitates a crimped or swaged connection to cable 486. End connector 490 may fit within an interrupted portion or slot 493 to rotate about pin 497 through hole 492. Pin 497 may be fixedly secured within holes 498 within pivot boss 495.

Figure 15:
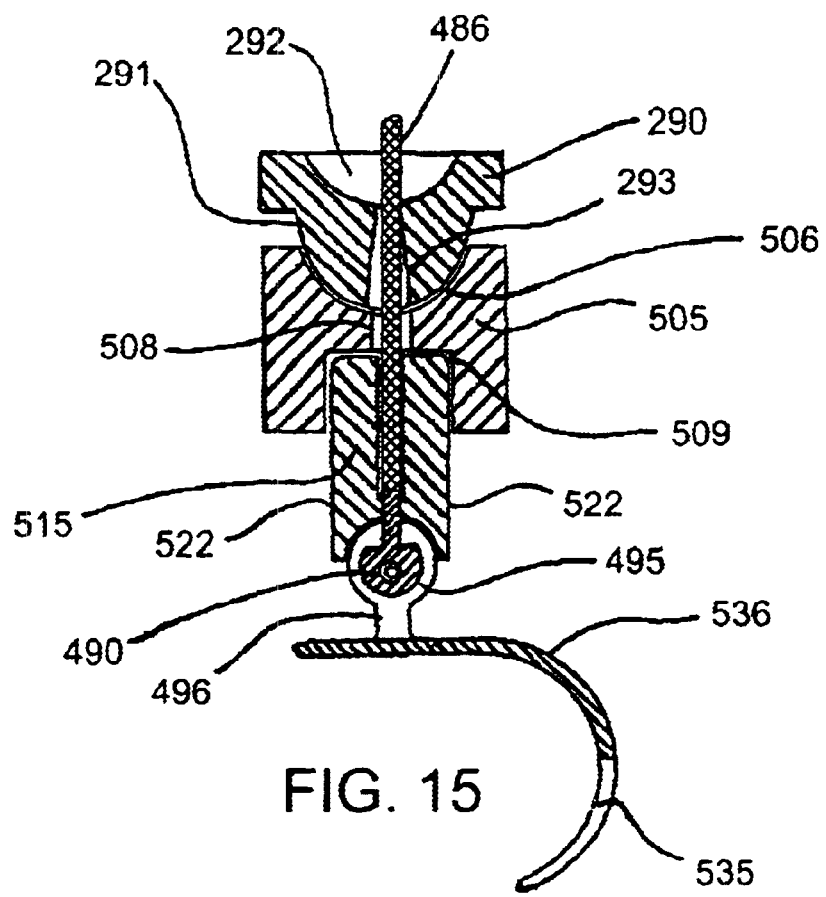
FIG. 15 is a cross-sectional view illustrating an alternative distal connection of a support member to a stabilizer foot.
Figure 16:
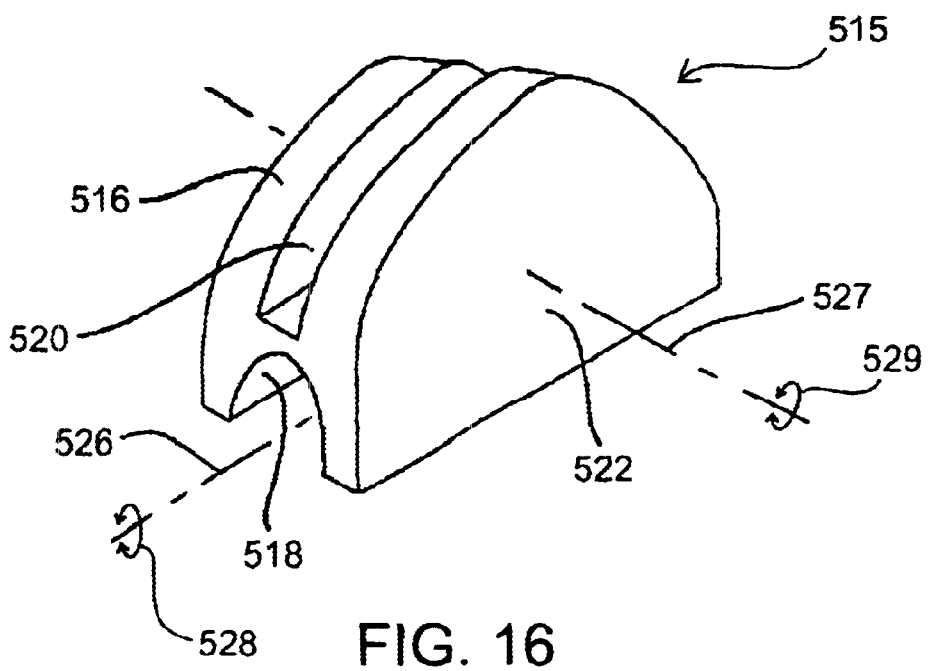
FIG. 16 is a perspective view illustrating one of the distal link components of the distal connection of FIG. 15.
Figure 17:
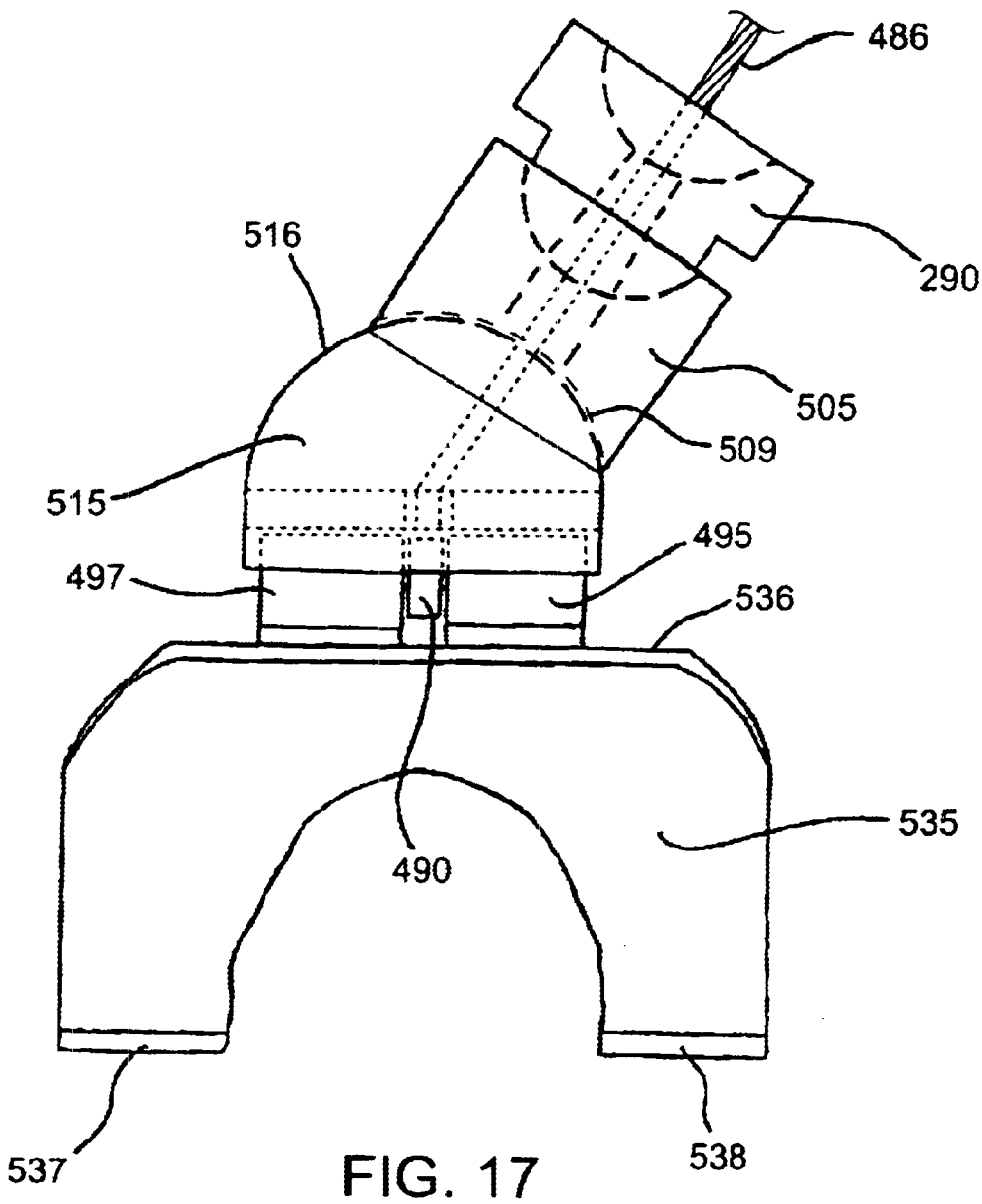
FIG. 17 is a front plan view illustrating the distal connection of FIG. 15 in an articulated relative to the support member.

This connection allows stabilizer foot 325 to be rotationally articulated about pivot boss 495 over a wide range of motion. Additional articulation of stabilizer foot 325 is limited to those degrees of freedom and range of motion provided by the ball and socket joints formed along the multiple links of support member 480. If desired, one or more additional degrees of freedom may be provided having an extended range of motion over the basic ball and socket joints provided by links 290 of support member 480. FIGS. 15–17 illustrate a distal connection to a stabilizer foot which provides an additional degree of rotational freedom over the single rotational joint of the prior embodiment.

The distal connection is shown in cross-section in FIG. 15. Stabilizer foot 535 again has pivot boss 495 having at least one cylindrical outer surface for rotating with a cooperating mating surface and an interruption or slot in which end connector 490 may be secured in the manner described above, preferably to a raised base portion 536. In a preferred embodiment, pivot boss 495 is connected to link 290 of support member 480 by way of first and second distal links 505 and 515. Preferably, pivot boss 495 and second distal link 515 are cooperatively engaged to provide a first rotational degree of freedom about a first axis and second distal link 515 and first distal link 505 are cooperatively engage to form a second rotational degree of freedom about a second axis. The first and second axes are preferably substantially perpendicular, but could be at any desired angle depending on the articulation desired for stabilizer foot 535 relative to support member 480.

A preferred second distal link is illustrated in FIG. 16. Second distal link 515 has a cylindrical pivot surface 518 adapted to receive pivot boss 495, forming a rotational joint about axis 526 as indicated by arrow 528. Second distal link 515 also has an arcuate upper profile 516 which is preferably adapted to engage mating arcuate channel 509 of first distal link 505. Arcuate channel 509 is adapted to slide along arcuate profile 516 generally about axis 527 as indicated by arrow 529. Second distal link 509 preferably has sides 522 which may be securely captured within arcuate channel 509. The configuration of second distal link 515 provides sufficient contact area for secure frictional engagement yet has a relatively thin width which does not impinge outward towards the surgical working area above first and second contact members 537 and 538.

Cable 486 is routed through openings 293 of multiple links 290, through central opening 508 of first distal link 505, through second distal link 515 and rotatably secured at the center of pivot boss 495 using a pin or the like. Second distal link has a slot or channel 520 to provide clearance for cable 486 as first distal link 505 is articulated relative to second distal link 515. An articulate position of first distal link 505 relative to second distal link 515 is illustrated in FIG. 17. As with the previous embodiments, each of the articulating joints along cable 486 may be frictionally locked by applying an appropriate tension to cable 486.

Regardless of the particular configuration of the stabilizer foot and the distal connection used to secure the stabilizer foot to the support member 480, the method of using the tissue stabilizer assembly 400 is essentially the same. An access opening is created to provide access to the tissue structure to be stabilized. Preferably, the access opening is created through the sternum using a sternal retractor having opposing blades, at least one or which having a rail member, such as rail 60.

Next, tissue stabilizer assembly 400 may be brought to engage rail 60. Rail grips 471 and 472 of tissue stabilizer assembly 460 are positioned to loosely engage rail 60. Tissue stabilizer assembly 400 may be traversed along rail 60 to a desired position, where rail grips 471 and 472 may be caused to frictionally lock or grip rail 60, preferably by rotating hinge member 412 using cam member 445.

Stabilizer foot 325 may be positioned at the target site, preferably with contact members 227 and 228 on each side of a target coronary artery on the surface of the beating heart. To optimize access to the surgical site, the position of support member 480 may be adjusted if desired by articulating links 290 or by articulation mount body 422 relative to mount base 421. Stabilizer foot 325 may then be manually engaged with the surface of the heart as desired to effectuate the desired stabilization. This may involve manually applying a desired amount of manual compression or, if the stabilizer foot so constructed, it may involve engaging the surface of the heart using negative pressure, adhesive tape, or other suitable instrumentality.

With the stabilizer foot in place and engaged as desired, knob 414 may be rotated in the appropriate direction to mechanically or frictionally lock both the in-line articulating joints provided along cable 486 as well as the articulating joint or joints provided between mount body 422 and the stable support, in this case retractor rail 60. If the surgical site is sufficiently stabilized, the surgical procedure can be performed.

For greater stabilization, stabilizer foot 325 may optionally have additional connections for securing additional support members, such posts as described with reference to stabilizer foot 125 or balls 232 and 234 as described above with reference to stabilizer foot 225. In that case, one or more additional support members, preferably having mount assemblies adapted to be secured to real 260; may be further attached to the stabilizer foot, adjusted as necessary and locked in place to further minimized motion at the target surgical site.

While certain embodiments are illustrated in the drawings and described herein, it will be apparent to those skilled in the art that many modifications can be made to the embodiments without departing from the inventive concepts herein described. For purposes of illustration only, the principles of the present invention has been primarily described with reference to stabilizing a beating heart during a coronary artery bypass procedure but may readily be applied to other types surgical procedures not specifically described. Many other uses are well-known in the art, and the concepts described herein are equally applicable to those other uses. Further, it is contemplated that the different components of the various exemplar embodiments described above can be combined to achieve any desirable construction. Accordingly, the invention is not to be restricted except by the claims which follow.

What is claimed is:

1. An apparatus for stabilizing a portion of a patient's heart comprising:
   a stabilizer foot adapted to engage the surface of the heart;
   a first support member having a distal end connected to said stabilizer foot at a first distal articulating joint and a proximal end connected to a stable support at first proximal articulating joint; and
   a second support member having a distal end adapted to be connected to said stabilizer foot at a second distal articulating joint and a proximal end connected to a stable support at a second proximal articulating joint.

2. The apparatus of claim 1 wherein said stable support is a retractor.

3. The apparatus of claim 2 wherein said first distal articulating joint is a ball and socket joint.

4. The apparatus of claim 3 wherein said second distal articulating joint is a rotational joint.

5. The apparatus of claim 1 wherein said first support member comprises a distal link, a proximal link, and a plurality of interconnecting links therebetween, each of said interconnecting links having a ball-shaped end and a socket-shaped end, said ball-shaped ends of said interconnecting links being cooperatively engaged with said socket-shaped ends of adjacent interconnecting links thereby forming articulating ball joints between adjacent interconnecting links.

6. The apparatus of claim 5, wherein each of said interconnecting links has a central hole and said first support member further comprises a cable having a distal end connected to said distal link and a proximal end, said cable routed through said central holes in said interconnecting links, whereby applying a tensile force to said proximal end of said cable frictionally locks said articulating ball joints between adjacent interconnecting links.

7. The apparatus of claim 6 wherein said first support member has a length of greater than about 6.5 inches and an average diameter of less than about 0.5 inches.

8. The apparatus of claim 7 wherein said length of said first support member is between about 7.0 inches and about 9.0 inches.

9. The apparatus of claim 1 further comprising a third support member having a distal end connected to said stabilizer foot at a third distal articulating joint and a proximal end connected to a stable support at a third proximal articulating joint.

10. The apparatus of claim 1 wherein said stabilizer foot has at least one textured contact surface adapted to frictionally engage the surface of the heart.

11. The apparatus of claim 10 wherein said stabilizer foot has a first contact surface and second contact surface, said second contact surface being spaced apart from and oriented substantially parallel to said first contact surface.

12. The apparatus of claim 11 wherein said stabilizer foot has a first post extending above said first contact surface and a second post extending from said second contact surface.

13. The apparatus of claim 12 further comprising a third support member having a distal end connected to said first post and a fourth support member having a distal end connected to said second post.

14. The apparatus of claim 13 wherein said third support member has a proximal end connected to said stable support at a third proximal articulating joint and said fourth support member has a proximal end connected to said stable support at a fourth articulating joint.

15. The apparatus of claim 1 wherein said stabilizer foot is adapted to engage the surface of the heart using negative pressure.

16. An apparatus for stabilizing a portion of a patient's heart comprising:
    a stabilizer foot adapted to engage the surface of the beating heart, said stabilizer foot having a ball-shaped member and a post connecting said ball-shaped member to said stabilizer foot;
    a support member having a proximal end link, a distal end link, and a plurality of center links arranged end-to-end therebetween; said support member having a cable extending through said plurality of links, said cable having a proximal end and an distal end; said distal end link comprising a first member and a second member having at least first and second flexible portions defining a cavity therebetween for receiving said ball-shaped member, said first member having a bearing surface adapted to engage at least a portion of said second member to urge said first and second flexible portions together against said ball; and
    an instrument mount comprising a base and a body rotable about said base, said support member proximal link being connected to said instrument mount body,
    wherein said apparatus is adapted to lock said links and said support body and base and engage said ball-shaped member with a single user interface.

17. The apparatus of claim 16 wherein said first member has a bore adapted to receive at least a portion of said second member and said distal end of said cable being attached to said second member, said first and second flexible portions engaged by said bearing surface as said second member is pulled in a first direction towards said first member by operation of said cable.

18. The apparatus of claim 16 wherein said bearing surface is a frustoconical.

19. The apparatus of claim 16 wherein said instrument mount is attached to a stable support.

20. The apparatus of claim 16 further comprising:
    a retractor having opposing retractor blades for engaging opposite sides of an access incision;
    a mount base operably connected to said retractor;
    a mount body connected to said mount base at a first articulating joint along a first axis; said proximal end link being connected to said mount body along a second axis.

21. The apparatus of claim 20 wherein said first axis is angled relative to said second axis, said angle being between about 120 degrees and about 45 degrees.

22. The apparatus of claim 16, wherein said single user interface comprises a knob.

23. The apparatus of claim 22, further comprising a base post having a cam surface provided to close a positing of said base post relative to said mount body so as to lock said mount body and base.

24. A method for stabilizing a portion of a patient's heart comprising the steps of:
    creating an access opening into the thoracic cavity;
    providing a stabilizer device having a stabilizer foot operably connected to a support member, said support member having a flexible condition and a relatively rigid condition;
    with said support member in the flexible condition, positioning the stabilizer foot to engage the surface of the heart adjacent a coronary artery;
    causing said support member to assume the relatively rigid condition to thereby resist movement of said stabilizer foot;
    providing at least one additional support member having a distal end, said at least one additional support member having a flexible condition and a relatively rigid condition;

attaching said distal end to said stabilizer foot; and causing said at least one additional support member to assume the relatively rigid condition to thereby providing additional resistance against movement of said stabilizer foot.

25. The method of claim 24 wherein said access opening is created using a retractor.

26. The method of claim 25 further comprising the steps of attaching said support member to said retractor and attaching said at least one additional support member to said retractor.

27. An apparatus for stabilizing a portion of a patient's heart comprising:

a stabilizer foot adapted to engage the surface of the heart;

a first support member having a distal end connected to said stabilizer foot at a first distal articulating joint and a proximal end connected to a stable support at first proximal articulating joint; and a second support member having a distal end connected to a second distal articulating joint and a proximal end connected to a stable support at a second proximal articulating joint, wherein said stabilizer foot has a first contact surface and second contact surface, said second contact surface being spaced apart from and oriented substantially parallel to said first contact surface, at least one of said surfaces being adapted to frictionally engage the surface of the heart, and wherein said stabilizer foot has a first post extending above said first contact surface and a second post extending from said second contact surface.

28. The apparatus of claim 27 further comprising a third support member having a distal end connected to said first post and a fourth support member having a distal end connected to said second post.

29. The apparatus of claim 28 wherein said third support member has a proximal end connected to said stable support at a third proximal articulating joint and said fourth support member has a proximal end connected to said stable support at a fourth articulating joint.

30. An apparatus for stabilizing a portion of a patient's heart comprising:

a retractor having opposing retractor blades for engaging opposite sides of an access incision;

a mount base operably connected to said retractor;

a mount body connected to said mount base at a first articulating joint along a first axis;

a multiple link support member having a proximal end and a distal end, said proximal end operably connected to said mount body along a second axis;

a stabilizer foot operably connected to said distal end and adapted to engage the surface of the heart, wherein said retractor blade comprises a rail and said mount base is adapted to engage said retractor blade along said rail, and wherein said rail has first and second rail tabs extending therefrom and said mount base has first and second channels sized to engage said rail tabs.

31. The apparatus of claim 30 wherein said second channel is moveable relative to said first channel such that said first and second channels slidably engage said rail tabs when said second channel is in a first position and said channels frictionally grip said rail tabs when said second channel is in a second position.

32. The apparatus of claim 30, wherein said retractor blades are curved.

33. The apparatus of claim 30, wherein said first and second axes are set at an angle between about 45 and about 100 degrees to each other.

34. The apparatus of claim 33, wherein said first axis is substantially perpendicular to said second axis.

35. The apparatus of claim 34, wherein said first articulating joint is rotational about said first axis.

36. The apparatus of claim 30, wherein said first articulating joint is a ball and socket joint.

37. The apparatus of claim 30, wherein said stabilizer foot is adapted to engage the surface of the heart using negative pressure.

38. The apparatus of claim 30, wherein said stabilizer foot is adapted to engage the surface of the heart using at least one textured surface.

39. The apparatus of claim 38, wherein said stabilizer foot is adapted to engage the surface of the heart without using negative pressure.

40. The apparatus of claim 38, wherein said stabilizer foot is adapted to engage the surface of the heart only using said at least one textured surface.

41. An apparatus for stabilizing a portion of a patient's heart comprising:

a retractor having opposing retractor blades for engaging opposite sides of an access incision;

a mount base operably connected to said retractor;

a mount body connected to said mount base at a first articulating joint along a first axis;

a multiple link support member having a proximal end and a distal end, said proximal end operably connected to said mount body along a second axis; and a stabilizer foot operably connected to said distal end and adapted to engage the surface of the heart;

at least one of said retractor blades further comprising a rail and said mount base being adapted to engage said retractor blade along said rail, wherein said rail has first and second rail tabs extending therefrom and said mount base has first and second channels sized to engage said rail tabs.

42. The apparatus of claim 41 wherein said first axis is at an angle relative to said second axis, said angle being between about 120 degrees and about 45 degrees.

43. The apparatus of claim 42 wherein said angle is about 90 degrees.

44. The apparatus of claim 41 wherein said second channel is moveable relative to said first channel such that said first and second channels slidably engage said rail tabs when said second channel is in a first position and said channels frictionally grip said rail tabs when said second channel is in a second position.

45. The apparatus of claim 41 wherein said multiple link support member comprises a distal link, a proximal link, and a plurality of interconnecting links therebetween, each of said interconnecting links having a ball-shaped end and a socket-shaped end, said ball-shaped ends of said interconnecting links being cooperatively engaged with said socket-shaped ends of adjacent interconnecting links thereby forming articulating ball joints between adjacent interconnecting links.

46. The apparatus of claim 45 wherein said stabilizer foot has a ball-shaped member extending therefrom and wherein said distal link has a mating cavity adapted to receive said ball-shaped member.

* * * * *

UNITED STATES PATENT AND TRADEMARK OFFICE
CERTIFICATE OF CORRECTION

PATENT NO. : 6,626,830 B1
DATED : September 30, 2003
INVENTOR(S) : Califiore et al.

It is certified that error appears in the above-identified patent and that said Letters Patent is hereby corrected as shown below:

Column 16,
Line 28, please delete the number "2" and insert -- 210 --;
Line 28, before the word "pre-attached" insert -- typically --;

Column 24,
Line 48, please delete the word "positing" and insert -- position --.

Signed and Sealed this

Twenty-seventh Day of April, 2004

JON W. DUDAS
*Acting Director of the United States Patent and Trademark Office*